United States Patent
Furstner et al.

(10) Patent No.: US 9,233,362 B2
(45) Date of Patent: Jan. 12, 2016

(54) MOLYBDENUM AND TUNGSTEN METAL COMPLEXES AND USE THEREOF AS PRECATALYSTS FOR OLEFIN METATHESIS

(75) Inventors: Alois Furstner, Mulheim an der Ruhr (DE); Johannes Heppekausen, Mulheim an der Ruhr (DE)

(73) Assignee: Studiengesellschaft Kohle MBH, Mulheim (DE)

( * ) Notice: Subject to any disclaimer, the term of this patent is extended or adjusted under 35 U.S.C. 154(b) by 156 days.

(21) Appl. No.: 14/001,811

(22) PCT Filed: Feb. 23, 2012

(86) PCT No.: PCT/DE2012/100047
§ 371 (c)(1),
(2), (4) Date: Nov. 11, 2013

(87) PCT Pub. No.: WO2012/116695
PCT Pub. Date: Sep. 7, 2012

(65) Prior Publication Data
US 2014/0296516 A1    Oct. 2, 2014

(30) Foreign Application Priority Data
Feb. 28, 2011 (DE) .................... 10 2011 012 629 U

(51) Int. Cl.
| | | |
|---|---|---|
| B01J 31/12 | (2006.01) | |
| C07F 11/00 | (2006.01) | |
| C07C 67/347 | (2006.01) | |
| C07D 223/12 | (2006.01) | |
| C07D 307/79 | (2006.01) | |
| C07F 7/18 | (2006.01) | |
| B01J 31/18 | (2006.01) | |
| B01J 31/22 | (2006.01) | |

(52) U.S. Cl.
CPC .............. B01J 31/12 (2013.01); C07C 67/347 (2013.01); C07D 223/12 (2013.01); C07D 307/79 (2013.01); C07F 7/1804 (2013.01); C07F 11/00 (2013.01); B01J 31/1805 (2013.01); B01J 31/1815 (2013.01); B01J 31/2265 (2013.01); B01J 2231/543 (2013.01); B01J 2531/64 (2013.01); B01J 2531/66 (2013.01)

(58) Field of Classification Search
CPC ...... B01J 31/12; C07C 67/347; C07F 7/1804; C07D 307/79; C07D 223/12
USPC ........................................................ 540/604
See application file for complete search history.

(56) References Cited

U.S. PATENT DOCUMENTS
6,121,473 A    9/2000 Schrock et al.
2008/0119678 A1    5/2008 Hock et al.
2011/0015430 A1    1/2011 Schrock et al.
2011/0077421 A1    3/2011 Schrock et al.
2013/0144102 A1    6/2013 Fuerstner et al.

FOREIGN PATENT DOCUMENTS
WO    2008066754    6/2008
WO    2009094201    7/2009
WO    WO2011/007742    8/2011

OTHER PUBLICATIONS

Tsai et al., 'Facile Synthesis of Trialkoxymolybdenum (VI) alkylidyne complexes for Alkyne Metathesis', Organmetallics 2000, vol. 19, No. 25, 5260-5262.
Heppekausen et al., 'Practical New Sulyloxy-Based alkyne metathesis Catalysts with Optimized Activity and Selectivity Profiles', J Am Chem Soc, 2010, vol. 132, No. 32, 11045-11057.
Extended European Search Report dated Nov. 6, 2013 for 13001297.4.
Schrock, 'Recent Advances in High Oxidation State Mo and W Imido Alkylidene Chemistry', Chemical Reviews, vol. 109 No. 8, Mar. 13, 2009.
'Marinescu et al., 'Ethenolysis Reactions Catalyzed by Imido alkylinene Monoaryloxide Monopyrrolide (MAP) Complexes of Molybdenum', Journal of the American Chemical Society, ACS Publications, US, vol. 131, No. 31, Aug. 12, 2009, pp. 10840-10841.
Yu et al., 'Enol Ethers as Substrates for Efficient Z—and Enantioselective Ring-Opening/Cross-Metathesis Reactions Promoted by Steriogenic-at-Mo Complexes: Utility in Chemical Synthesis and Mechanistic Attributes', Journal of the American Chemical Society, vol. 134, No. 5, Jan. 24, 2012, pp. 2788-2799.
Bailey et al., 'Evaluation of Molybdenum and Tungsten Metathesis Catalysts for Homogeneous Tandem Alkane Metathesis', Organometallics, vol. 28, No. 1, Dec. 12, 2008, pp. 355-360.
Marinescu et al., 'Simple Molybdenum (IV) Olefin Complexes of the Type Mo (NR) (X) (Y) (olefin)', Organometiallics, vol. 29, No. 24, Dec. 2, 2010, pp. 6816-6828.

(Continued)

Primary Examiner — Paul V Ward
(74) Attorney, Agent, or Firm — Stoel Rives LLP

(57) ABSTRACT

The invention relates to metal complexes of general formula (I) and to a method for the production thereof, in which M, $R^1$, $R^2$, $R^3$, X and Y in addition to $R^a$, $R^b$, $R^c$, $R^d$, $R^e$, $R^f$, $R^g$, $R^h$ can have the meanings defined in the claims. Said metal complexes form air-stable compounds and are suitable as precatalysts in the olefin metathesis.

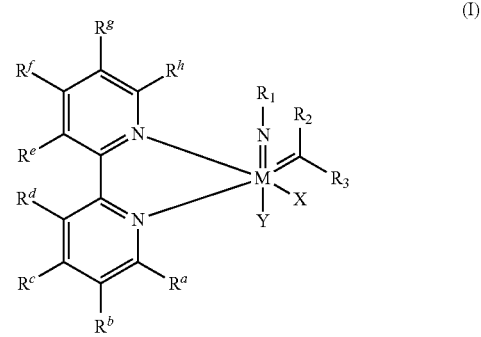

10 Claims, No Drawings

(56) References Cited

OTHER PUBLICATIONS

Yu et al., 'Synthesis of Macrocyclic Natural Products by Catalyst-Controlled Stereoselective Ring-Closing Metathesis', Nature, vol. 479, No. 7371, Nov. 2, 2011, pp. 89-93.

Jiang et al., 'Highly Z-Selective Metathesis Homocoupling of Terminal Olefins', Journal of the American Chemical Society ACS Publications, US, vol. 131, No. 46, Nov. 25, 2009, pp. 16630-16631.

Lee et al., 'Endo-Selective Enyne Ring-Closing Metathesis Promoted by Steriogenic-at-Mo Monoalkoxide and Momoaryloxide Complexes. Efficient Synthesis of Cyclic Dienes Not Accessible Through Reactions with Ru Carbenes', Journal of the American Chemical Society, vol. 131, No. 30, Jul. 6, 2009, pp. 10652-10661.

U.S. Appl. No. 14/209,313, filed Mar. 13, 2014, Ondi et al.

Fox et al., 'Synthesis of Five-and Six-Coordinate Alkylidene Complexes of the Type Mo (CHR)(NAr) [OCMe(CF3)2Sx and Their Use as Living ROMP Initiators or Wittig Reagents', American Chemical Society, Organometallics, 1993, 12, pp. 759-768.

Totland et al., 'Ring Opening Metathesis Polymerization with Binaphtholate or Bibhenolate Complexes of Molybdenum', American Chemical Society, Macromolecules, 1996, 29, pp. 6114-6125.

MOLYBDENUM AND TUNGSTEN METAL COMPLEXES AND USE THEREOF AS PRECATALYSTS FOR OLEFIN METATHESIS

CROSS-REFERENCE TO RELATED APPLICATIONS

This application is a national stage application under 35 U.S.C. §371 of International Application No. PCT/DE2012/100047, titled MOLYBDENUM AND TUNGSTEN METAL COMPLEXES AND USE THEREOF AS PRECATALYSTS FOR OLEFIN METATHESIS, filed Feb. 23, 2012, which claims priority to German Application No. 102011012629.5, filed Feb. 28, 2011, all of which are hereby incorporated by reference in their entireties.

The present invention relates to metal complexes of molybdenum or tungsten, to methods for the manufacture thereof and to the use thereof as pre-catalysts for olefin metathesis reactions.

Alkene metathesis is the mutual trans-alkylidenation of alkenes according to Scheme 1 (Ivin, K. J.; Mol, J. C. *Olefin Metathesis and Metathesis Polymerization*, Academic Press, San Diego, 1997).

Scheme 1. General Principle of the Alkene Metathesis

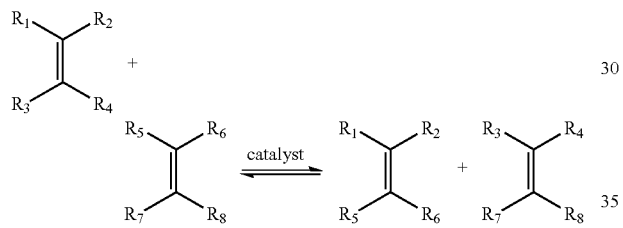

Alkene metathesis reactions are catalyzed by metal compounds which may be present in the reaction mixture in homogeneous or heterogeneous form. The real catalytically active species are so-called Schrock-alkylidenes which may be produced in situ or ex situ. (Schrock, R. R. *Chem. Rev.* 2002, 102, 145). Besides alkylidene complexes of ruthenium, frequently Schrock-alkylidenes of molybdenum and tungsten are used which are characterized by a high or very high catalytic activity (Schrock, R. R., *Chem. Rev.* 2009, 109, 3211; Schrock, R. R.; Hoveyda, A. H. Angew. *Chem. Int. Ed.* 2003, 42, 4592); some Schrock-alkylidenes of molybdenum and tungsten are also commercially available. However, contrary to ruthenium alkylidenes (Vougioukalakis, G. C; Grubbs, R. R. *Chem. Rev.* 2010, 110, 1746) Schrock-alkylidenes of molybdenum and tungsten are very sensitive towards air and humidity, as a rule, and thus must be handled and reacted under inert conditions. They are decomposed by air and humidity within a short time; in most cases, this decomposition occurs within some seconds. Due to this high sensitivity, the use of Schrock-alkylidenes of molybdenum and tungsten requires special working techniques and partly a considerable complex equipment and preparative work.

Schrock-alkylidenes of molybdenum and tungsten may be stabilized by adduct formation with donor ligands. As donor ligands mostly ethers and phosphanes were used in the literature, in some cases also nitrogen ligands such as pyridine, pyridine derivatives or quinuclidine (Schrock, R. R., Crowe, W. E.; Bazan, G. C; DiMare, M.; O'Regan, M. B.; Schofield, M. H. *Organometallics* 1991, 10, 1832); however, ether adducts remain very sensitive to air and humidity. The stability of the adducts with phosphane, quinuclidine or pyridine depends on the donor power and the size of the selected phosphanes, of the quinuclidine or the selected pyridines as well as from the electrophilic character of the selected Schrock-alkylidene. NMR measurements show that the complex formation in solution is partially reversible already at room temperature. In no case it has been reported about the stability of the formed adducts towards air and/or humidity.

By means of complex formation of Schrock-alkylidenes by means of hydrotris(pyrazolyl)borate or hydrotris(3,5-dimethylpyrazolyl)borate, however, adducts may be produced with are stable against air. However, neither hydrotris(pyrazolyl)borate nor hydrotris(3,5-dimethylpyrazolyl)borate may be detached from these adducts by means of addition of Lewis acids such as, for example, $AlCl_3$, so that the original Schrock-alkylidene complex may not be re-released. Rather, the addition of Lewis acids such as, for example, $AlCl_3$, results in the reaction with other ligands of the formed adduct and thus to the formation of one or several new, structurally not completely clarified compounds (J. M. Boncella et al., *J. Am. Chem. Soc.* 1991, 113, 7066; *Organometallics* 1992, 11, 2342; *Organometallics* 1993, 12, 2814; *J. Organomet. Chem.* 1995, 485, 37).

In one case a bipyridine adduct of a Schrock-methylidene complex 1 as such has been described (Fox, H. H.; Lee, J.-K.; Park, L. Y.; Schrock, R. R. *Organometallics* 1993, 12, 759) in which the alkylidene moiety is a terminal moiety, i.e. is not further substituted. A further reaction of the methylidene complex 1 has not been described.

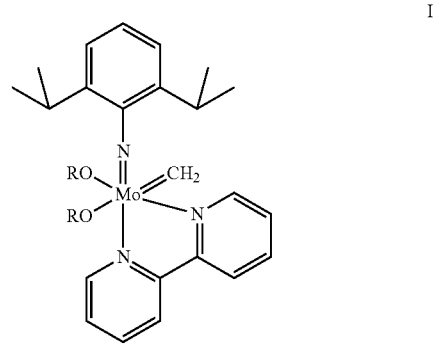

R = C(Me)(CF$_3$)$_2$

Surprisingly, it now has been discovered that Schrock-alkylidenes of molybdenum and tungsten having a non-terminal alkylidene moiety can be stabilized by means of complex formation (adduct formation) with bidentate nitrogen ligands such as, for example, 1,10-phenanthroline or 2,2'-bipyridine (2,2'-dipyridyl), respectively derivatives thereof, insofar that they may be handled without particular precautionary measure at air and may be stored over a long period of time at air at room temperature without decomposition without particular precautionary measure. In some cases, these adducts are storable at air at room temperature over months without decomposition. However, even under the common reaction conditions for metathesis reactions, these complexes show no noteworthy catalytic activity. Contrary to the hitherto existing knowledge of the prior art, however, it has been surprisingly discovered that from the mentioned complexes (adducts) which are made from Schrock-alkylidenes of molybdenum and tungsten and bidentate nitrogen ligands by means of suitable additives, the catalytically active Schrock-alkylidenes can be re-released in an inert solvent in an unchanged manner and in good yields; thereby, the high catalytic activity of these Schrock-alkylidenes is restored. The method described in this invention for the manufacture and use of air stable adducts and the release of the active species by reaction of said adducts with suitable additives considerably simplifies the handling and use of Schrock-alkylidenes of molybdenum and tungsten since neither special working techniques nor a particular complex equipment is necessary.

Accordingly, object of the present invention are metal-complexes of the general formula I

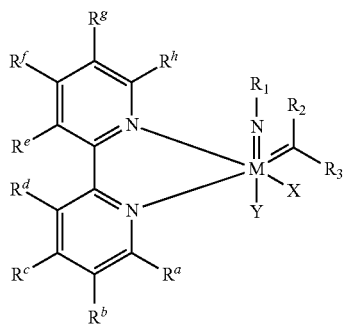

in which
M is Mo or W,
$R^1$ is $C_1$-$C_{12}$ alkyl, 5- to 18-membered aryl, which in turn may be substituted with one or more of $C_1$-$C_{12}$ alkyl, 5- to 18-membered aryl, $C_1$-$C_{12}$-alkoxy, di($C_1$-$C_4$-alkyl)amino, halogen, trifluoromethyl, cyano, nitro residues, which may be the same or which may be different, the substituents X, Y may be the same or may be different and may be independently selected from one another from: halogen, methanesulfonyloxy, trifluoromethanesulfonyloxy, benzenesulfonyloxy, toluenesulfonyloxy, pyrrolyl, $C_1$-$C_{12}$-alkyloxy, 5- to 18-membered aryloxy, tri($C_1$-$C_{12}$-alkyl)silyloxy, di($C_1$-$C_{12}$-alkyl)($C_6$-$C_{18}$-aryl)silyloxy, ($C_1$-$C_{12}$-alkyl)di($C_6$-$C_{18}$-aryl)silyloxy, tris($C_1$-$C_{12}$-alkyloxy)silyloxy, which in turn may be substituted with one or more of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, nitro residues, which may be the same or which may be different,
$R^2$ is H, $C_1$-$C_{12}$-Alkyl, 5- to 18-membered aryl, which in turn may be substituted with one or more of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, nitro residues, which may be the same or which may be different,
$R^3$ is $C_1$-$C_{12}$-alkyl, 5- to 18-membered aryl, which in turn may be substituted with one or more of $C_1$-$C_{12}$-alkyl, 5- to 18-membered aryl, $C_1$-$C_{12}$-alkyloxy, di($C_1$-$C_4$alkyl)amino, halogen, trifluoromethyl, cyano, nitro residues, which may be the same or which may be different,
$R^a$, $R^b$, $R^c$, $R^d$, $R^e$, $R^f$, $R^g$, $R^h$ may be the same or may be different and may be independently selected from H, halogen, nitro, cyano, trifluoromethyl, $C_1$-$C_{12}$-alkoxycarbonyl, $C_1$-$C_{12}$-alkyl, 5- to 18-membered aryl, $C_1$-$C_{12}$-alkyloxy, di-($C_1$-$C_4$-alkyl)amino, which in turn may be substituted with one or more of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, nitro residues, which may be the same or which may be different, or residues $R^d$ and $R^e$ may be connected to one another while forming a 5- to 8-membered ring.

Residues $R^d$ and $R^e$ may also be connected to one another while forming a 5- to 8-membered ring and may together form a residue $R^{48}$, which means $CR^{49}R^{50}$, $CR^{51}$=$CR^{52}CR^{53}R^{54}$—$CR^{55}R^{56}$, $CR^{57}R^{58}$—$CR^{59}R^{60}$—$CR^{61}R^{62}$, $CR^{62}R^{63}$=$CR^{64}R^{65}$—$CR^{66}R^{67}$, $CR^{69}R^{70}$—$CR^{71}R^{72}$—$CR^{73}R^{74}$—$CR^{75}CR^{76}$, $CR^{77}$=$CR^{78}$—$CR^{79}R^{80}$—$CR^{81}CR^{82}$ and/or $CR^{83}R^{84}$—$CR^{85}$=$CR^{87}$—$CR^{88}CR^{89}$ in which $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}R^{68}$, $R^{69}$, $R^{70}$, $R^{71}$, $R^{72}$, $R^{73}$, $R^{74}$, $R^{75}$, $R^{76}$, $R^{77}$, $R^{78}$, $R^{79}$, $R^{80}$, $R^{81}$, $R^{82}$, $R^{83}$, $R^{84}$, $R^{85}$, $R^{86}$, $R^{87}$, $R^{88}$ and $R^{89}$ are independently selected from one another, respectively, and may have the same meaning as $R^a$.

The metal complexes of Formula I form compounds which are stable at air. It is assumed that the stabilization is performed by complex formation at suitable nitrogen ligands.

Preferred compounds according to the present invention are characterized by the following formula 2

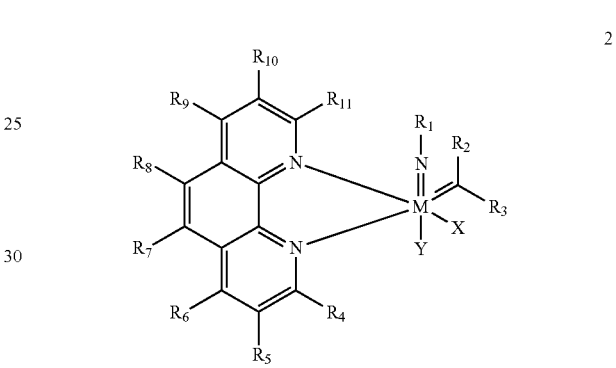

wherein
M, $R^1$, $R^2$, $R^3$, X and Y are defined above,
the substituents $R^4$, $R^5$, $R^6$, $R^7$, $R^8$, $R^9$, $R^{10}$, $R^{11}$ may be the same or may be different and may be independently selected from one another from: H, halogen, nitro, cyano, trifluoromethyl, $C_1$-$C_{12}$-alkoxycarbonyl, $C_1$-$C_{12}$-alkyl, 5- to 18-membered aryl, $C_1$-$C_{12}$-alkyloxy, di-($C_1$-$C_4$-alkyl)amino, which in turn may be substituted with one or more of $C_1$-$C_{12}$-alkyl, 5- to 18-membered aryl, $C_1$-$C_{12}$-alkyloxy, di-($C_1$-$C_4$-alkyl) amino, halogen, trifluoromethyl, cyano, nitro residues, which may be the same or which may be different.

The following terms mean in the scope of the invention:
"$C_1$-$C_{12}$-alkyl" a non-branched, branched or cyclic alkyl residue having from 1 to 12 carbon atoms.
"5- to 18-membered aryl" a monocyclic, bicyclic or tricyclic carbocyclic or heterocyclic aromatic residue which in turn may bear from 0 to 5 substituents selected from the list: $C_1$-$C_{12}$-alkyl, $C_1$-$C_{12}$-alkoxy, di($C_1$-$C_4$-alkyl)amino, 5- to 18-membered aryl, halogen, cyano, nitro.
"Di-($C_1$-$C_4$-alkyl)amino" an amino group having two non-branched, branched or cyclic alkyl substituents which have from 1 to 4 carbon atoms, respectively, and which may be the same or which may be different.
"Halogen" encompasses in the scope of the invention fluorine, chlorine, bromine and iodine.

Preferred alkyl residues in the scope of this invention are non-branched, branched or cyclic alkyl residues having from 1 to 12 carbon atoms. Exemplarily and preferably are mentioned: methyl, trifluoromethyl, ethyl, n-propyl, isopropyl, hexafluoroisopropyl, n-butyl, iso-butyl, sec-butyl, tert-butyl, trifluoro-tert-butyl, hexafluoro-tert-butyl, nonafluoro-tertbutyl, 1-ethylpropyl, n-pentyl, n-hexyl, cyclopropyl, cyclobutyl, cyclopentyl, cyclohexyl and cycloheptyl, adamantyl.

Preferred aryl residues in the scope of this invention are: phenyl, naphthyl, anthryl, methylphenyl, dimethylphenyl, trimethylphenyl, ethylphenyl, diethylphenyl, isopropylphenyl, di(isopropyl)phenyl, tri(isopropyl)phenyl, tert-butylphenyl, di(tert-butyl)phenyl, methoxyphenyl, dimethoxyphenyl, trimethoxyphenyl, trifluoromethylphenyl, bis(trifluoromethyl)phenyl, fluorophenyl, difluorophenyl, chlorophenyl, dichlorophenyl, bromophenyl, iodophenyl, pentafluorophenyl, dimethylaminophenyl, phenylphenyl, diphenylphenyl, (methoxycarbonyl)phenyl), (ethoxycarbonyl)phenyl, (tert-butoxycarbonyl)phenyl; likewise preferred are heterocyclic aryl residues having up to two heteroatoms selected from N, O and/or S such as furyl, thienyl, thiazolyl, oxazolyl, indolyl, isothiazolyl, isoxazolyl, pyrazolyl, imidazolyl, pyridyl, primidinyl, pyridazinyl, pyrazinyl, benzofuranyl, benzothiophenyl, benzimidazolyl, carbazolyl.

Preferred di-($C_1$-$C_4$-alkyl)amino residues in the scope of this invention are the following di-$C_1$-$C_4$-alkylamino residues: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino and N-tert-butyl-N-methylamino.

Further preferred compounds in the scope of the present invention are complexes of general formula 3

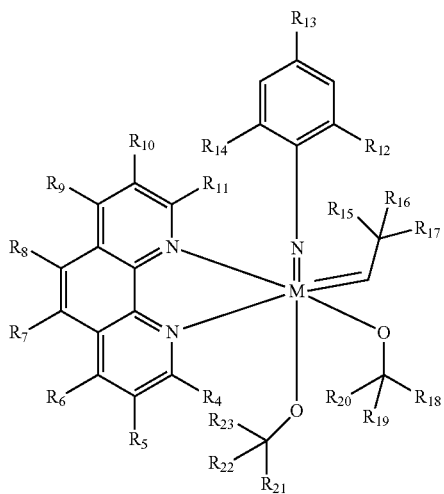

3 wherein
M=Mo, W,
the substituents $R^{12}$, $R^{13}$, $R^{14}$ may be the same or may be different and may be independently selected from: H, halogen, trifluoromethyl, methyl, ethyl, propyl, butyl, isopropyl, tert-butyl,
the substituents $R^{15}$, $R^{16}$, $R^{17}$ may be the same or may be different and may be independently selected from one another from: H, methyl, ethyl, propyl, phenyl,
the substituents $R^{18}$, $R^{19}$, $R^{20}$, $R^{21}$, $R^{22}$, $R^{23}$ may be the same or may be different and may be independently selected from one another from: H, methyl, trifluoromethyl,
the substituents $R^4$, $R^5$, $R^6$, $R^7$, $R^8$, $R^9$, $R^{10}$, $R^{11}$ may be the same or may be different and may be independently selected from one other from: H, $C_1$-$C_6$-alkyl, $C_1$-$C_6$-alkyloxy, $C_1$-$C_6$-alkyloxycarbonyl, phenyl, halogen, nitro.

Likewise preferred compounds in the scope of the present invention are complexes of the general formula 4

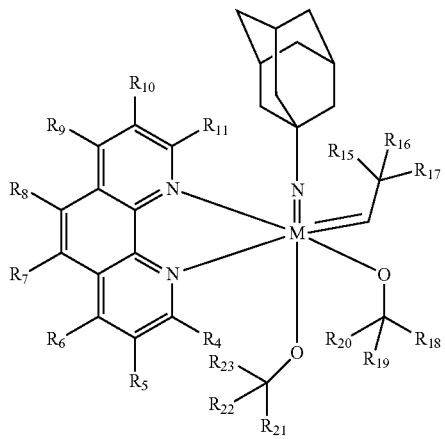

4 wherein
M=Mo,
the substituents $R^{15}$, $R^{16}$, $R^{17}$ may be the same or may be different and may be independently selected from one another from: H, methyl, ethyl, propyl, phenyl,
the substituents $R^{18}$, $R^{19}$, $R^{20}$, $R^{21}$, $R^{22}$, $R^{23}$ may be the same or may be different and may be independently selected from one another from: H, methyl, trifluoromethyl,
the substituents $R^4$, $R^5$, $R^6$, $R^7$, $R^8$, $R^9$, $R^{10}$, $R^{11}$ may be the same or may be different and may be independently selected from one another from: H, $C_1$-$C_6$-alkyl, $C_1$-$C_6$-alkyloxy, $C_1$-$C_6$-alkyloxycarbonyl, phenyl, halogen, nitro.

Examples for preferred 1,10-phenanthrolines which may be used in the scope of this invention as ligands for stabilizing Schrock-alkylidene complexes of molybdenum or tungsten are: 1,10-phenanthroline, 4-methyl-1,10-phenanthroline, 5-methyl-1,10-phenanthroline, 2,9-dimethyl[1,10]phenanthroline, 5,6-dimethyl-1,10-phenanthroline, 5-chloro[1,10]phenanthroline, 4,7-dichloro-1,10-phenanthroline, 4,7-dichloro-1,10-phenanthroline, 3,4,7,8-tetramethyl-1,10-phenanthroline, 4,7-diphenyl[1,10]phenanthroline, 2,9-dimethyl-4,7-diphenyl[1,10]phenanthroline, 5-nitro-1,10-phenanthroline, 4,7-dimethoxy-1,10-phenanthroline.

Particular preferred compounds in the scope of the present invention are complexes of the general formula 5-8

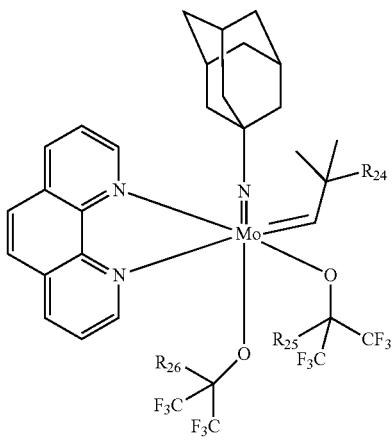

5

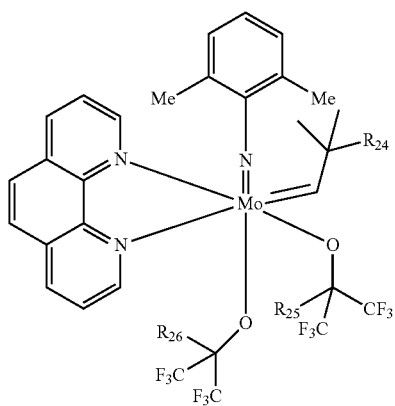

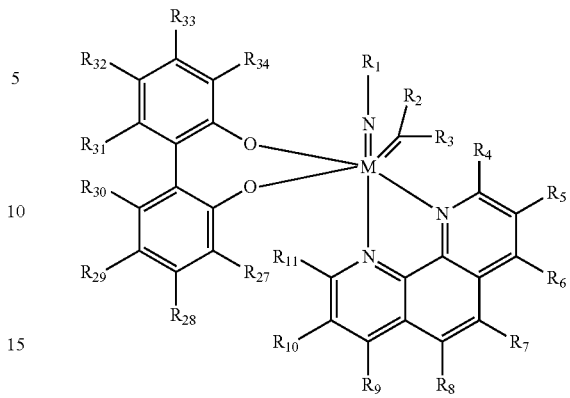

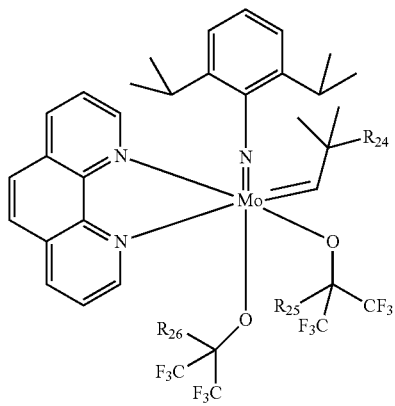

wherein

M, $R^1$, $R^2$, $R^3$ and $R^4$, $R^5$, $R^6$, $R^7$, $R^8$, $R^9$, $R^{10}$, $R^{11}$ are defined above, the substituents $R^{27}$, $R^{28}$, $R^{29}$, $R^{30}$, $R^{31}$, $R^{32}$, $R^{33}$, $R^{34}$ may be the same or may be different and may be independently selected from one another from: H, halogen, nitro, cyano, trifluoromethyl, $C_1$-$C_{12}$-alkoxycarbonyl, $C_1$-$C_{12}$-akly, 5- to 8-membered aryl, $C_1$-$C_{12}$-alkyloxy, di-($C_1$-$C_4$-alkyl)amino, which in turn may be substituted with one or more of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, nitro residues, which may be the same or may be different.

Complexes of the general formula 10, methods for the manufacture thereof and the use thereof as pre-catalysts for the alkene metathesis are likewise an object of the present invention,

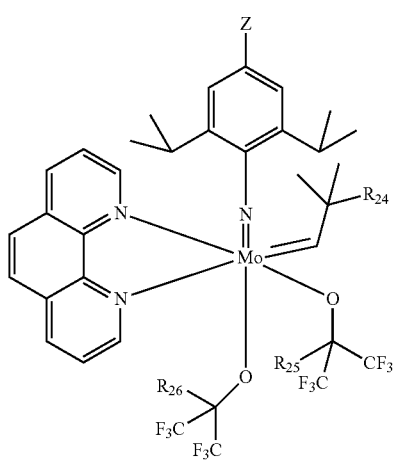

wherein
$R^{24}$=Me, Ph
$R^{25}$, $R^{26}$=H, Me, $CF_3$
Z=methyl, iso-propyl, halogen.

Complexes of the general formula 9, methods for the manufacture thereof and the use thereof as pre-catalysts for the alkene metathesis are likewise an object of the present invention,

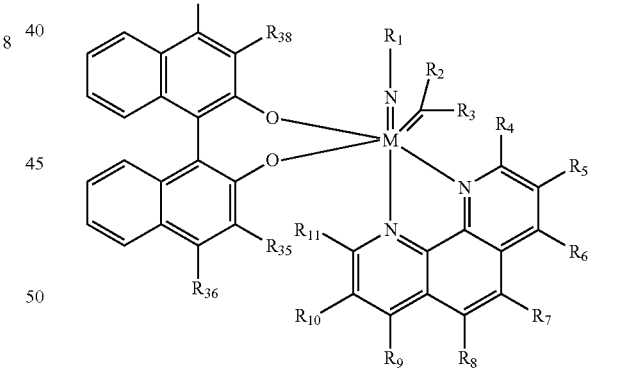

wherein

M, the substituents $R^1$, $R^2$, $R^3$, $R^4$, $R^5$, $R^6$, $R^7$, $R^8$, $R^9$, $R^{10}$ and $R^{11}$ are defined above and the substituents $R^{35}$, $R^{36}$, $R^{37}$, $R^{38}$ may be the same or may be different and may be independently selected from one another from: H, halogen, nitro, cyano, trifluoromethyl, $C_1$-$C_{12}$-alkyl, 5- to 18-membered aryl, $C_1$-$C_{12}$-alkyloxy, di-($C_1$-$C_4$-alkyl)amino, tri($C_1$-$C_{12}$-alkyl)silyl, di($C_1$-$C_{12}$-alkyl)($C_6$-$C_{18}$-aryl)silyl, ($C_1$-$C_{12}$-alkyl)di($C_6$-$C_{18}$-aryl)silyl, which in turn may be substituted with one or more of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, nitro residues, which may be the same or may be different.

Examples for particularly preferred compounds in the scope of the present invention are complexes of the general formulas 11-16,
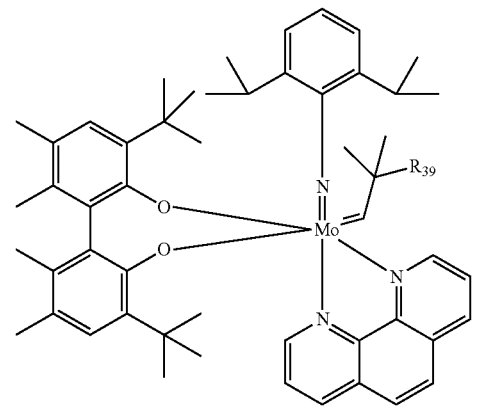
11
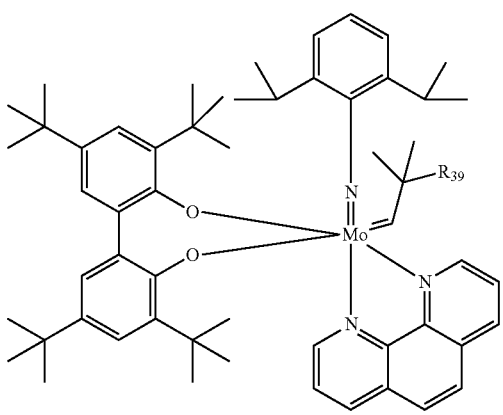
12
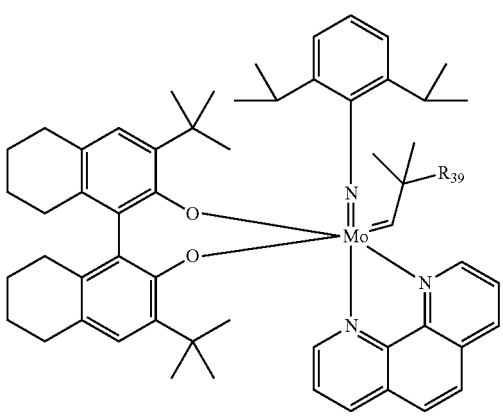
13
-continued
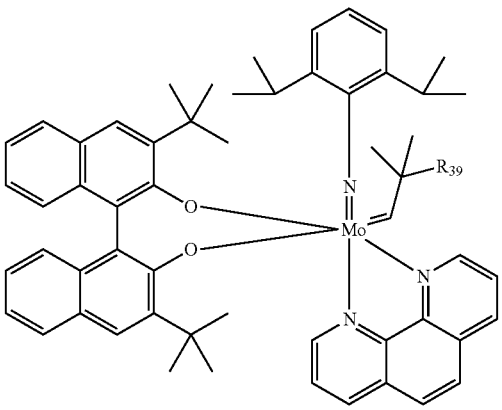
14
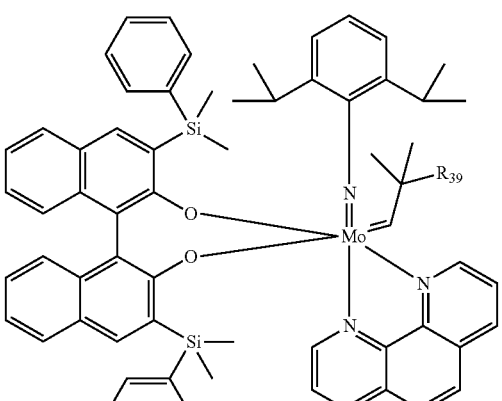
15
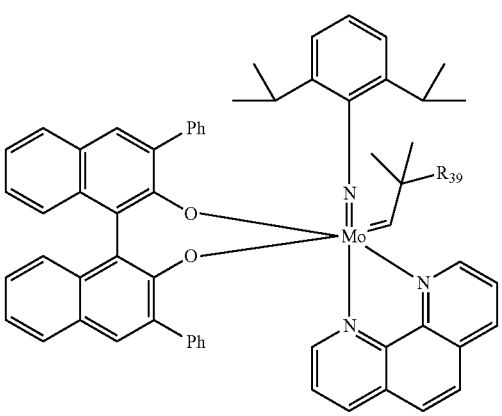
16
Ph = Phenyl
wherein
$R^{39}$=Me, phenyl.
Complexes of general formula 17, methods for the manufacture thereof as well as the use thereof as pre-catalysts for the alkene metathesis are likewise an object of the present invention,

17

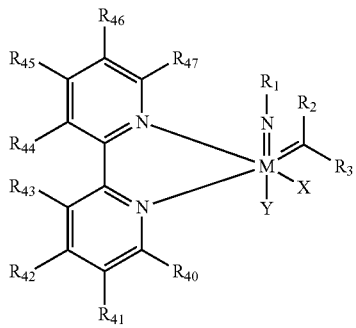

wherein
M=Mo, W,
the substituent $R^1$ may be selected from: $C_1$-$C_{12}$-alkyl, 5- to 18-membered aryl, which in turn may be substituted with one or more of $C_1$-$C_{12}$-alkyl, 5- to 18-membered aryl, $C_1$-$C_{12}$-alkyloxy, di-($C_1$-$C_{12}$-alkyl)amino, halogen, trifluoromethyl, cyano, nitro residues, which may be the same or may be different,
the substituents X, Y may be the same or may be different and may be independently selected from one another from: halogen, methanesulfonyloxy, trifluoromethanesulfonyloxy, benzenesulfonyloxy, pyrrolyl, $C_1$-$C_{12}$-alkyloxy, 5- to 18-membered aryloxy, tri($C_1$-$C_{12}$-alkyl)silyloxy, di($C_1$-$C_{12}$-alkyl)($C_6$-$C_{18}$-aryl)silyloxy, ($C_1$-$C_{12}$-alkyl)di($C_6$-$C_{18}$-aryl)silyloxy, tris($C_1$-$C_{12}$-alkyloxy)silyloxy, which in turn may be substituted with one or more of $C_1$-$C_{12}$-alkyl, 5- to 18-membered aryl, $C_1$-$C_{12}$-alkoxy, di-($C_1$-$C_4$-alkyl)amino, halogen, trifluoromethyl, cyano, nitro residues, which may be the same or may be different,
the substituent $R^2$ may be selected from the residues: H, $C_1$-$C_{12}$-alkyl, 5- to 18-membered aryl, wherein each of said residues may be in turn substituted with one or more of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, nitro residues, which may be the same or may be different,
the substituent $R^3$ may be selected from the residues: $C_1$-$C_{12}$-alkyl, 5- to 18-membered aryl, wherein each of said residues may be in turn substituted with one or more of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, nitro residues, which may be the same or may be different,
the substituents R40, R41, R42, R43, R44, R45, R46, R47 may be the same or may be different and may be independently selected from one another from: H, halogen, nitro, cyano, trifluoromethyl, C1-C12-alkoxycarbonyl, C1-C12-alkyl, 5- to 18-membered aryl, C1-C12-alkyloxy, di-(C1-C4-alkyl)amino, which in turn may be substituted with one or more of C1-C12-alkyl, 5- to 18-membered aryl, C1-C12-alkyloxy, di-(C1-C4-alkyl)amino, halogen, trifluoromethyl, cyano, nitro residues, which may be the same or may be different.

Preferred compounds in the scope of the present invention are complexes of the general formula 18

18

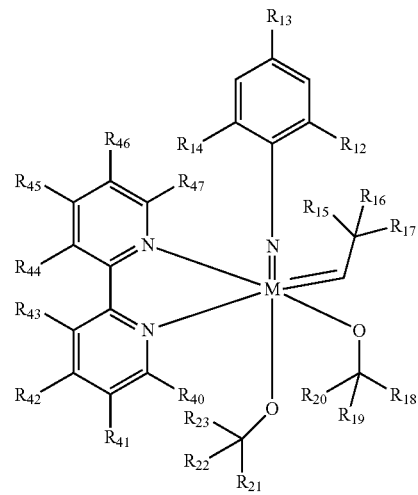

wherein
M=Mo, W,
the substituents $R^{12}$, $R^{13}$, $R^{14}$ may be the same or may be different and may be independently selected from one another from: H, halogen, trifluoromethyl, methyl, ethyl, propyl, butyl, iso-propyl, tert-butyl,
the substituents $R^{15}$, $R^{16}$, $R^{17}$ may be the same or may be different and may be independently selected from one another from: H, methyl, ethyl, propyl, phenyl,
the substituents $R^{18}$, $R^{19}$, $R^{20}$, $R^{21}$, $R^{22}$, $R^{23}$ may be the same or may be different and may be independently selected from one another from: H, methyl, trifluoromethyl,
the substituents $R^{40}$, $R^{41}$, $R^{42}$, $R^{43}$ $R^{44}$, $R^{45}$, $R^{46}$, $R^{47}$ may be the same or may be different and may be independently selected from one another from: H, $C_1$-$C_6$-alkyl, $C_1$-$C_6$-alkyloxy, $C_1$-$C_6$-alkyloxycarbonyl, phenyl, halogen, nitro.

Likewise preferred compounds in the scope of the present invention are complexes of the general formula 19

19

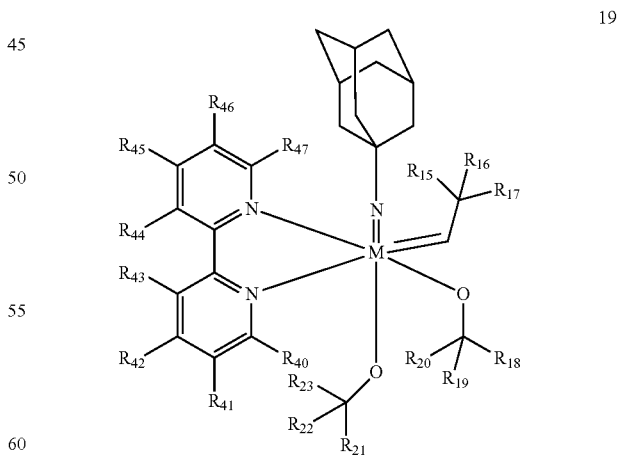

wherein
M=Mo,
the substituents $R^{15}$, $R^{16}$, $R^{17}$ may be the same or may be different and may be independently selected from one another from: H, methyl, ethyl, propyl, phenyl, the substituents $R^{18}, R^{19}, R^{20}, R^{21}, R^{22}, R^{23}$ may be the same or may be different and may be independently selected from one another from: H, methyl, trifluoromethyl, the substituents $R^{40}, R^{41}, R^{42}, R^{43}, R^{44}, R^{45}, R^{46}, R^{47}$ may be the same or may be different and may be independently selected from one another from: H, $C_1$-$C_6$-alkyl, $C_1$-$C_6$-alkyloxy, $C_1$-$C_6$-alkyloxycarbonyl, phenyl, halogen, nitro.

Examples for preferred 2,2'-bipyridines (2,2' dipyridyles) which may be used in the scope of this invention as ligands for stabilizing Schrock-alkylidene complexes of molybdenum or tungsten are: 2,2'-bipyridine, 5,5'-dimethyl-2,2'-dipyridyl, 4,4'-dimethyl-2,2'-dipyridyl, 6,6'-dimethyl-2,2'-dipyridyl, 4-4'-dimethoxy-2-2'-bipyridine, 2,2'-biquinoline, 4,4'-di-tert-butyl-2,2'-dipyridyl, 2,2'-bipyridinyl-4,4'-dicarboxylic acid dimethylester, 4,4'-diphenyl-2,2'-dipyridyl, 6,6'-dibromo-2,2'-dipyridyl, 4,4'-dinonyl-2,2'-dipyridyl, 2,2'-biquinolinyl-4,4'-dicarboxylic acid dibutylester, 2,2'-biquinolinyl-4,4'-dicarboxylic acid diheptylester, 6-methyl-2,2'-dipyridyl, 2-(2-pyridinyl)quinoline, 2-pyridin-2-yl-4-pyrrolidin-1-yl-quinoline, 4-piperidin-1-yl-2-pyridin-2-yl-quinoline, 4-morpholin-4-yl-2-pyridin-2-yl-quinoline.

Particularly preferred compounds in the scope of the present invention are complexes of the general formula 20-23

20

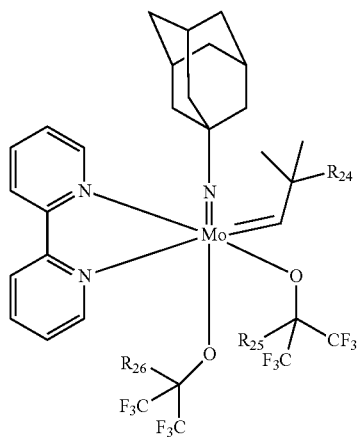

21

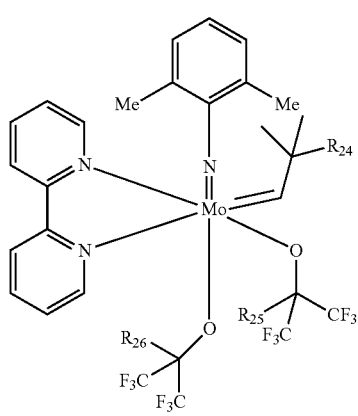

22

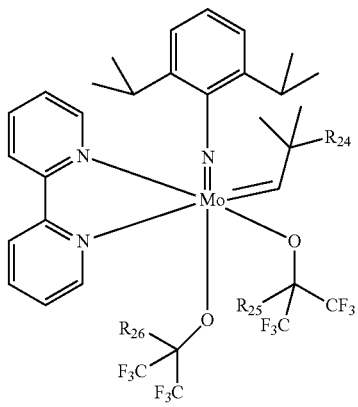

23

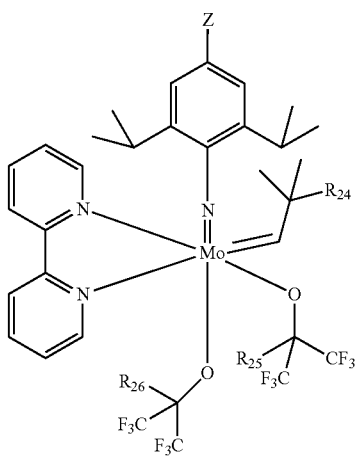

wherein
$R^{24}$=Me, Ph
$R^{25}, R^{26}$=H, Me, $CF_3$
Z=methyl, iso-propyl, halogen.

Complexes of the general formula 24, methods for the manufacture thereof and the use thereof as pre-catalysts for the alkene metathesis are likewise an object of the present invention,

24

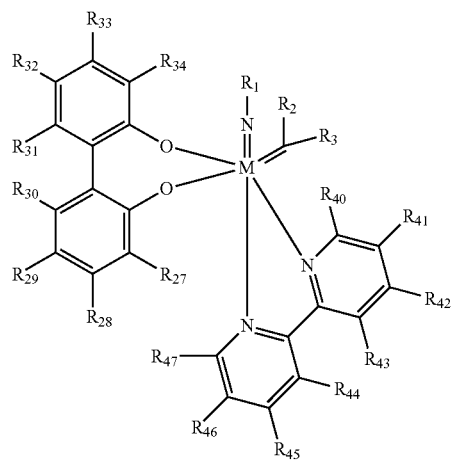

wherein

M, $R^1$, $R^2$ and $R^3$ as well as $R^{27}$, $R^{28}$, $R^{29}$, $R^{30}$, $R^{31}$, $R^{32}$, $R^{33}$, $R^{34}$, $R^{40}$, $R^{41}$, $R^{42}$, $R^{43}$, $R^{44}$, $R^{45}$, $R^{46}$ and $R^{47}$ are defined above.

Complexes of the general formula 25, methods for the manufacture thereof and the use thereof as pre-catalysts for the alkene metathesis are likewise an object of the present invention,

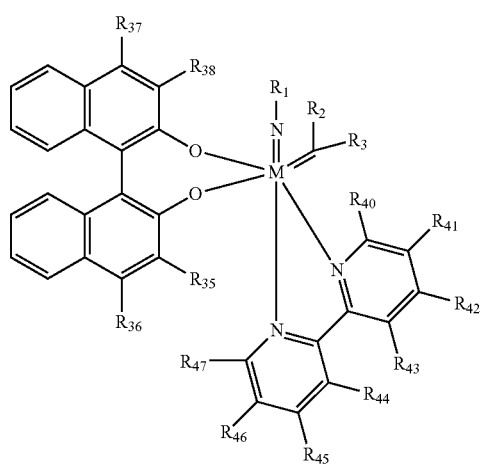

wherein

M, $R^1$, $R^2$ and $R^3$ as well as $R^{35}$, $R^{36}$, $R^{37}$, $R^{38}$, $R^{40}$, $R^{41}$, $R^{42}$, $R^{43}$, $R^{44}$, $R^{45}$, $R^{46}$ and $R^{47}$ are defined above.

Examples for particularly preferred compounds in the scope of the present invention are complexes of the general formulas 26-31

26

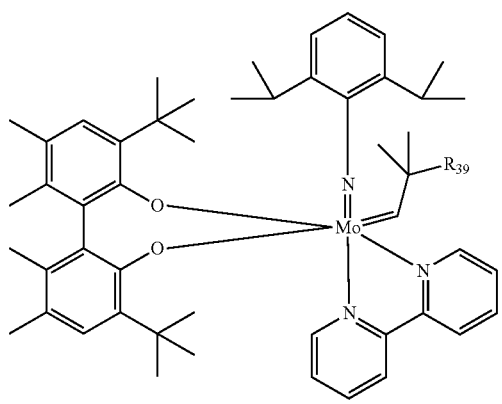

27

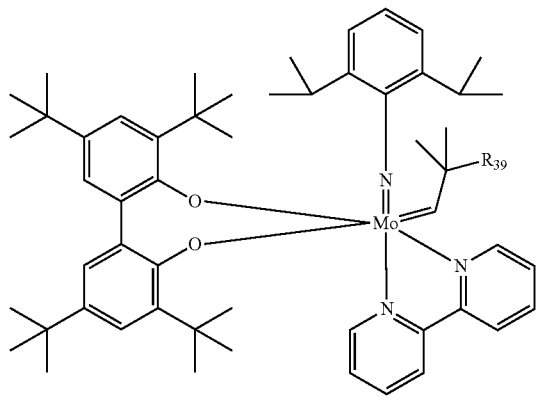

28

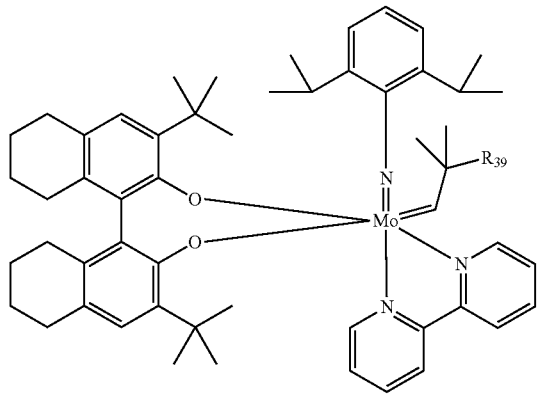

29

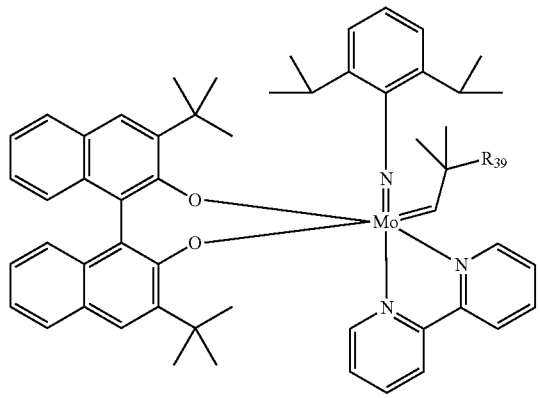

-continued

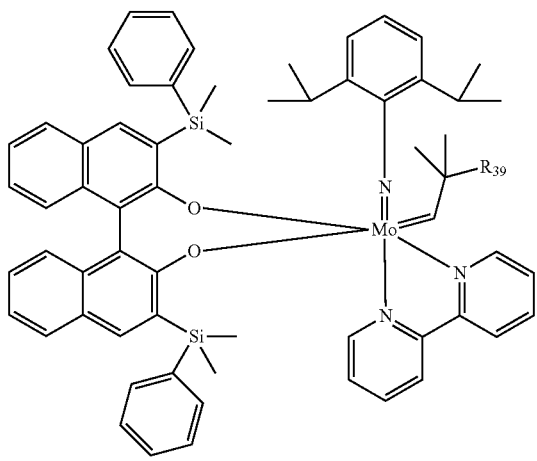

30

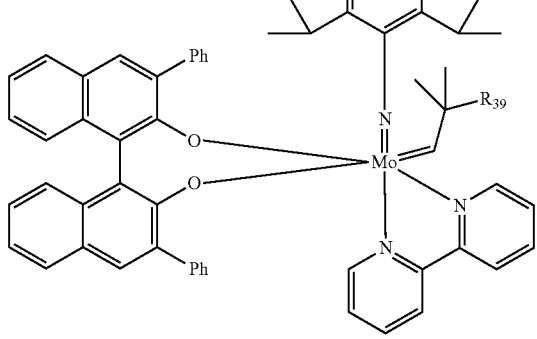

31

Ph = Phenyl wherein
R$^{39}$=Me, Phenyl.

A further object of the present invention is a method for the manufacture of compounds of general formulas I

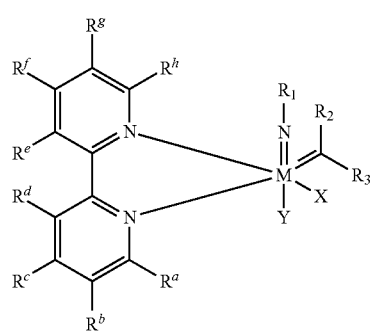
(I)

wherein
M, X, Y, R$^1$, R$^2$, R$^3$, R$^a$, R$^b$, R$^c$, R$^d$, R$^e$, R$^f$, R$^g$, R$^h$ are defined above,
in which a compound of formula 32

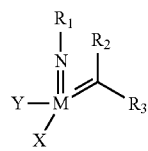
32 wherein
M, X, Y, R$_1$, R$_2$, R$_3$ are defined above,
is reacted with a compound of general formula II

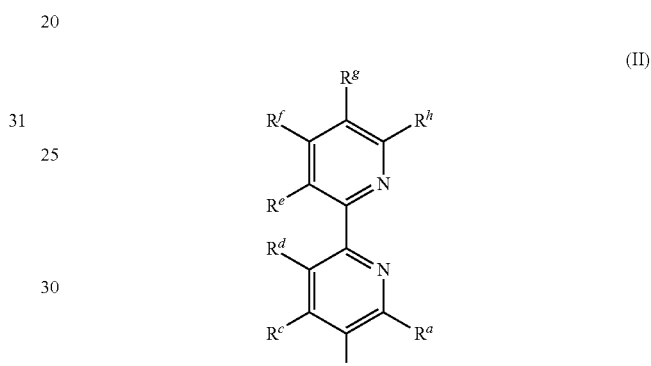
(II)

wherein
R$^a$, R$^b$, R$^c$, R$^d$, R$^e$, R$^f$, R$^g$, R$^h$ are defined above.

Scheme 2. Examples for the preparation of particularly preferred complexes.

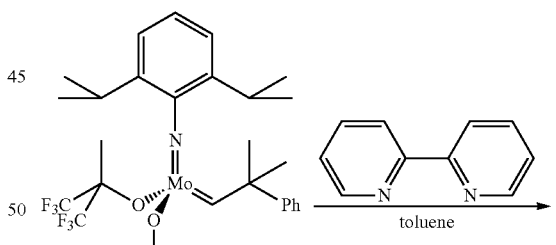
37

38

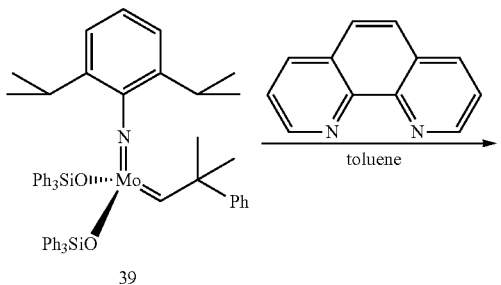

39

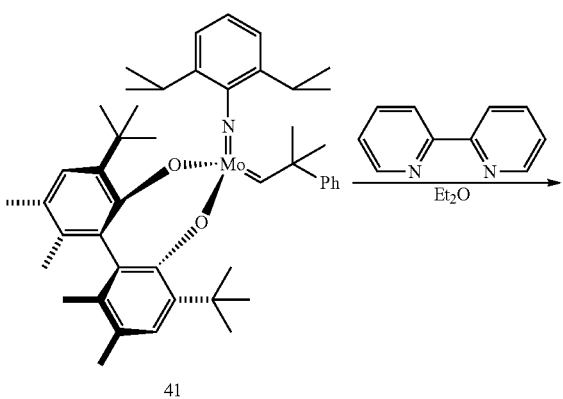

40

41

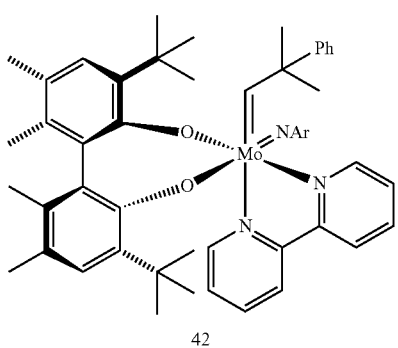

42

Examples for the manufacture of particularly complexes according to the mentioned method are shown in scheme 2 and are described in section "Examples" in detail.

A further object of the present invention is a method for the use of complexes of the formulas I, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 38, 40, 42, 43 as pre-catalysts for performing alkene metathesis reactions by activation with a suitable additive. In this method, a solution or a suspension of compound of formulas I, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 38, 40, 42, 43 is reacted in a suitable solvent with anhydrous metal salts or metal complexes as additives which in turn form stable 1,10-phenanthroline complexes, respectively 2,2'-bipyridine complexes. This activation is performed by means of decomplexing the respective 1,10-phenanthroline, respectively 2,2'-bipyridine ligands from molybdenum or tungsten while forming the respective 1,10-phenanthroline complexes, respectively 2,2'-bipyridine complexes of the used additives, which optionally remain in the reaction mixture or may be separated off from the mixture prior to the alkene metathesis. For this activation all anhydrous metal salts or metal complexes may be used, which form stable 1,10-phenanthroline complexes, respectively 2,2'-bipyridine complexes. Particularly preferred examples are mentioned in scheme 3 and in section "Examples".

Preferred additives are: $AlX_3$, $MnX_2$, $FeX_2$, $FeX_3$, $COX_2$, $CuX_2$, $ZnX_2$, $MgX_2$, $NiX_2$, $PdX_2$, $PtX_2$, $RuX_2$, $RuX_3$, $EuX_3$, with X=F, Cl, Br, I, acetylacetonate, sulfate, sulfonate, nitrate, acetate, trifluoroacetate, trifluoromethanesulfonate (triflate).

Particularly preferred additives are: $MgCl_2$, $MgBr_2$, $MgI_2$, $MnCl_2$, $MnBr_2$, $MnI_2$, $FeCl_3$, $AlCl_3$, $CuCl_2$, $ZnCl_2$, $ZnBr_2$, $ZnI_2$, $Zn(triflate)_2$, $Zn(trifluoroacetate)_2$.

Depending on the selected additive and adduct, the activation may be performed at different temperatures, preferably at temperatures between −20° C. and +140° C., particularly preferred at temperatures between 20° C. and 110° C. All solvents may be used as solvents which do not lead to the decomposition of the released Schrock-alkylidene complexes of molybdenum or tungsten; preferred solvents are hydrocarbons, halogenated hydrocarbons and ethers; particularly preferred are pentanes, hexanes, heptanes, octanes, petroleum ether, benzene, toluene, xylene, cumene, decalin, chlorobenzene, bromobenzene, fluorobenzene, trifluoromethylbenzene, dichlorobenzene, trichlorobenzene, dichloromethane, chloroform, carbon tetrachloride, 1,2-dichloroethane, tetrahydrofuran, 1,4-dioxane, dimethoxyethane, diethylether, tert-butylmethylether. Also mixtures of these solvents may be used.

Scheme 3. Example of the activation of a catalytically inactive adduct from a Schrock-alkylidene and 1,10-phenantroline (43) respectively 2,2'-bipyridine (38) while using ZnCl₂ as particularyl preferred additive in toluene as a particularly preferred solvent according to the present invention. If the reaction is performed in deuterated toluene, the release of the Schrock-alkylidene 37, which is catalytically active in the alkene metathesis, may be observed by $^1$H NMR spectroscopy.

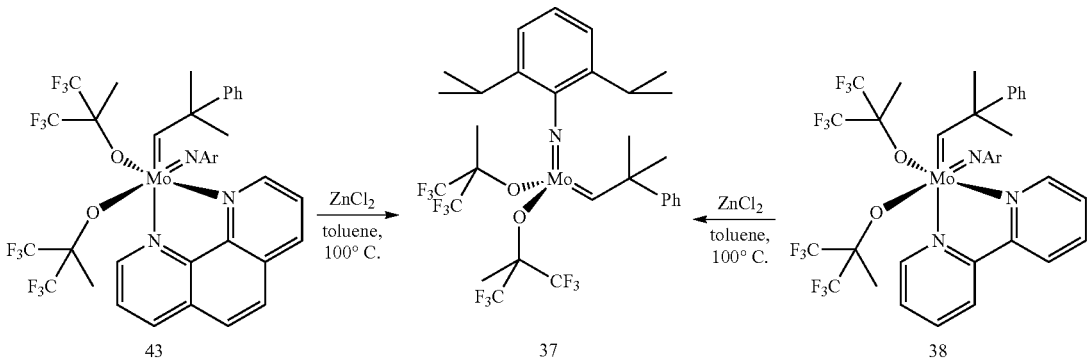

EXAMPLES

Abbreviations: phen=1,10-phenanthroline; bipy=2,2'-bipyridine; dme=1,2-dimethoxyethane; biphen=biphenyl-2,2'-diolate; TMS=trimethylsilyl; TBS=tert-butyldimethylsilyl; TBDPS=tert-butyldiphenylsilyl.

The 2,2'-bipyridine derivatives which are used for the preparation of the complexes were dissolved in toluene and the solution was dried over molecular sieve 5 Å (MS 5 Å). Subsequently, the molecular sieve was filtered off, the filtrate was concentrated and the remaining 2,2'-bipyridine derivative was kept under argon.

The 1,10-phenanthroline derivatives which were used for the preparation of the complexes, were either purified and dried by double sublimation in high vacuum or were dissolved in toluene and the solution was dried over molecular sieve 5 Å (MS 5 Å); subsequently, the toluene was distilled off in vacuo and the remaining 1,10-phenanthroline derivative was kept under argon.

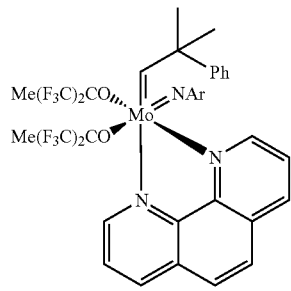

[Mo(CHCMe₂Ph)(NAr)(OCMe(CF₃)₂)₂(phen)](Ar=2,6-diisopropylphenyl).

A solution of [Mo(CHCMe₂Ph)(NAr)(OCMe(CF₃)₂)₂] (326 mg, 426 µmol) in toluene (3 mL) was added to a solution of 1,10-phenanthroline (77 mg, 426 µmol) in toluene (2 mL) and the mixture was stirred for one hour at room temperature. Subsequently, the formed precipitate was filtered off and was washed with cold toluene (approximately 2 mL). The combined filtrates were concentrated to approximately one third of the original volume and were subsequently cooled down to −40° C., what resulted in a second charge of complex. The charges were combined and were dried in vacuo. Yellow solid (384 mg, 95%). $^1$H NMR (400 MHz, CD₂Cl₂): δ=13.88 (s, 1H), 9.48 (dd, J=4.7, 1.6 Hz, 1H), 8.41 (dd, J=8.3, 1.6 Hz, 1H), 8.37 (dd, J=8.3, 1.6 Hz, 1H), 7.98 (dd, J=5.2, 1.3 Hz, 1H), 7.92 (d, J=8.9 Hz, 1H), 7.86-7.82 (m, 2H), 7.67 (dd, J=8.5, 1.0 Hz, 2H), 7.46 (t, J=8.1 Hz, 2H), 7.33 (t, J=7.3 Hz, 1H), 7.30 (dd, J=8.2, 5.6 Hz, 1H), 6.91 (br s, 1H), 6.80 (t, J=7.6 Hz, 1H), 6.71 (br s, 1H), 4.38 (br s, 1H), 3.13 (br s, 1H), 2.07 (s, 3H), 1.68 (s, 3H), 1.65 (s, 3H), 1.19 (br s, 6H), 0.85 (br s, 3H), 0.26 (s, 3H), −0.55 ppm (br s, 3H); $^{13}$C NMR (100 MHz, CD₂Cl₂): δ=309.6, 158.9, 150.5, 150.0, 149.6, 149.5, 145.8, 143.4, 139.3, 138.4, 138.0, 130.4, 129.9, 129.4, 128.7, 128.6, 127.9, 126.9, 126.7, 126.4, 126.3, 125.6, 125.1, 124.9, 80.1, 55.0, 32.0, 28.8, 28.2, 26.9, 26.6, 24.7, 24.3, 22.6, 21.5, 17.9, 17.6 ppm; $^{19}$F NMR (377 MHz, CD₂Cl₂): δ=−76.3 (q, J=10.3 Hz, 3F), −77.4 (m, 3F), −77.6 (q, J=10.3 Hz, 3F), −77.9 ppm (m, 3F); IR (film, cm$^{-1}$): 2966, 2868, 1578, 1424, 1296, 1214, 1163, 1105, 1070, 958, 844, 762, 727, 697.

This complex is intact according to $^1$H NMR for approx. 50% after storage for four weeks at room temperature at air.

FIG.1. Structure of [Mo(CHCMe₂Ph)(NAr)(OCMe(CF₃)₂)₂(phen)] (Ar = 2,6-diisopropylphenyl) in the solid state.

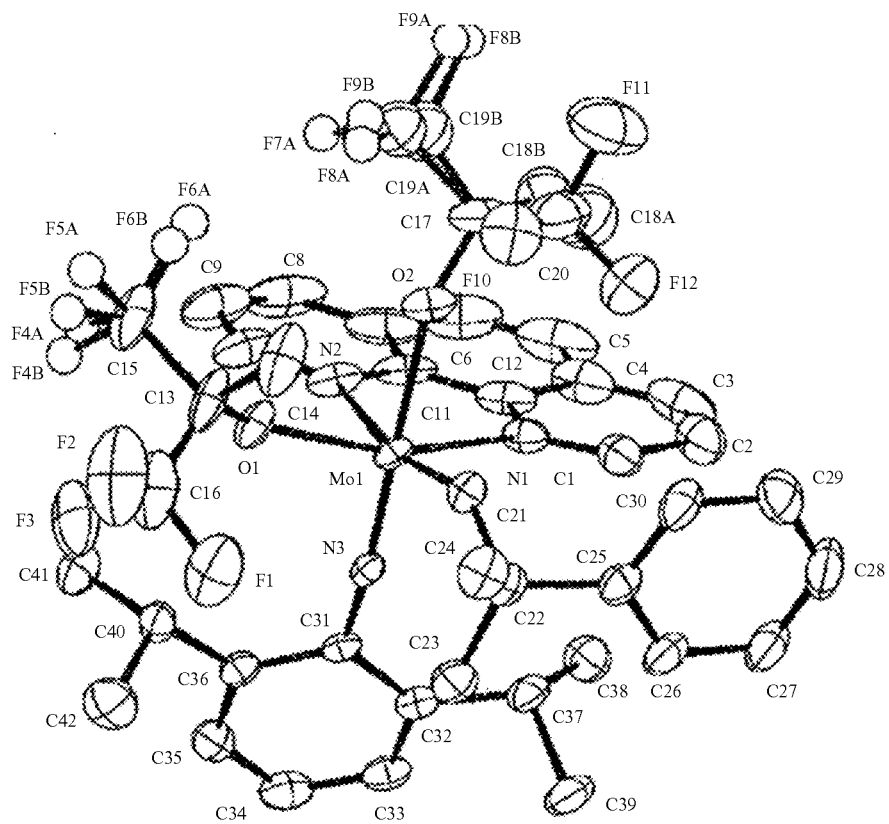

[Mo(CHCMe₂Ph)(NAr)(OCMe(CF₃)₂)₂(bipy)](Ar=2,6-diisopropylphenyl).

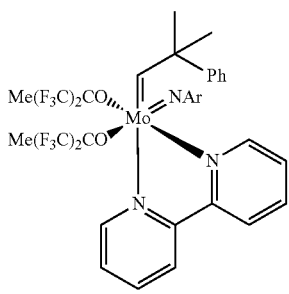

A solution of [Mo(CHCMe₂Ph)(NAr)(OCMe(CF₃)₂)₂] (360 mg, 470 μmol) in toluene (3 mL) was added to a solution of 2,2'-bipyridine (73 mg, 470 μmol) in toluene (2 mL) and the mixture was stirred for one hour at room temperature. Subsequently, the formed precipitate was filtered off and was washed with cold toluene (approx. 2 mL). The combined filtrates were concentrated to approx. a third of the original volume and subsequently cooled down to −40° C., which resulted in a second charge of complex. The charges were combined and were dried in vacuo. Yellow solid (382 mg, 88%). $^1$H NMR (400 MHz, CD₂Cl₂): δ=13.74 (s, 1H), 9.22 (dd, J=5.1, 1.6 Hz, 1H), 8.02 (d, J=8.0 Hz, 1H), 7.97 (d, J=8.1 Hz, 1H), 7.92-7.84 (m, 2H), 7.76 (d, J=4.6 Hz, 1H), 7.62 (d, J=8.2 Hz, 2H), 7.54 (ddd, J=7.4, 5.2, 1.3 Hz, 1H), 7.41 (t, J=7.4 Hz, 2H), 7.28 (tt, J=7.3, 1.2 Hz, 1H), 6.96 (ddd, J=7.4, 5.6, 1.3 Hz, 1H), 9.92 (br s, 1H), 6.88 (t, J=7.0 Hz, 1H), 6.84 (br s, 1H), 4.19 (br s, 1H), 3.16 (br s, 1H), 2.02 (s, 3H), 1.63 (s, 3H), 1.61 (s, 3H), 1.24 (br s, 3H), 1.12 (br s, 3H), 0.81 (br s, 3H), 0.55 (s, 3H), −0.09 ppm (br s, 3H); $^{13}$C NMR (100 MHz, CD₂Cl₂): δ=309.0, 159.7, 154.9, 153.1, 151.5, 150.3, 149.9, 149.7, 149.6, 148.0, 140.0, 139.2, 128.5, 126.8, 126.4, 126.3, 126.2, 122.8, 121.4, 80.1, 54.8, 31.9, 28.7, 28.5, 26.9, 26.1, 25.0, 24.5, 22.6, 17.7 ppm; $^{19}$F NMR (377 MHz, CD₂Cl₂): δ=−76.4 (q, J=10.3 Hz, 3F), −77.1 (q, J=10.3 Hz, 3F), −77.4 (m, 3F), −77.7 ppm (m, 3F); IR (film, cm⁻¹): 2968, 2868, 1599, 1443, 1296, 1210, 1165, 1078, 1024, 955, 757, 697.

This complex is intact according to $^1$H NMR after storage for four weeks at room temperature at air and exhibited no realizable decomposition (<5%).

FIG. 2. Structure of [Mo(CHCMe$_2$Ph)(NAr)(OCMe(CF$_3$)$_2$)$_2$(bipy)] (Ar = 2,6-diisopropylphenyl) in the solid state.

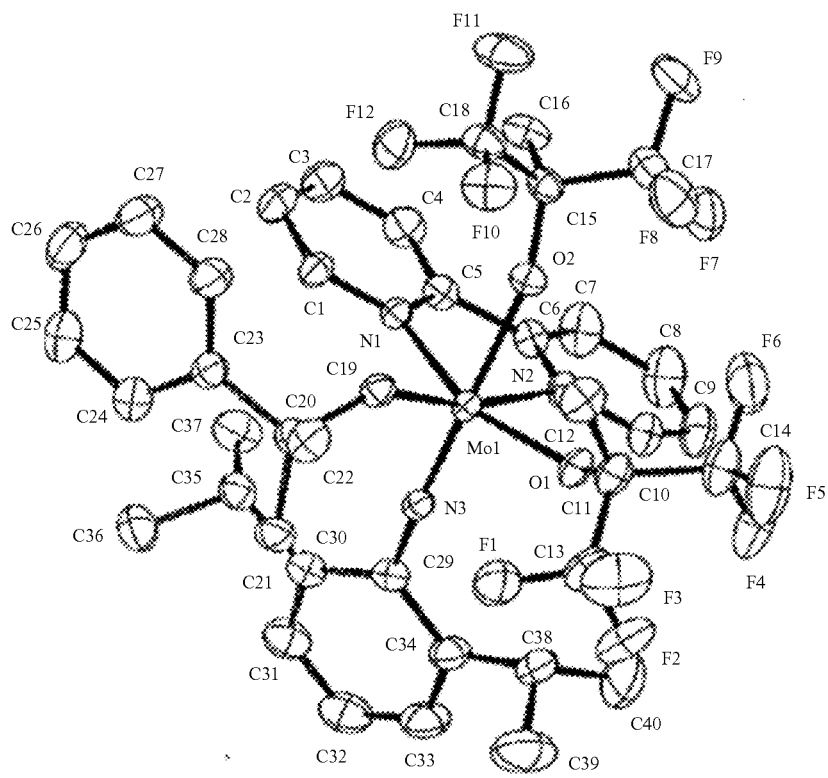

[Mo(CH-tBu)(NAr)(OSiPh$_3$)$_2$(phen)](Ar=2,6-diisopropylphenyl).

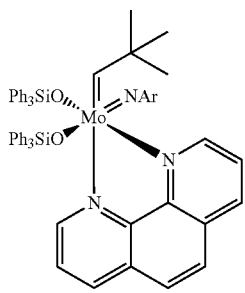

A solution of Ph$_3$SiOK (302 mg, 959 μmol) in toluene (5 mL) was added to a solution of [Mo(CH-tBu)(NAr)(OSO$_2$CF$_3$)$_2$(dme)](350 mg, 480 μmol) in toluene (5 mL) and the mixture was stirred for one hour at room temperature. Subsequently, the formed precipitate was filtered off and the filtrate was added to a solution of 1,10-phenanthroline (87 mg, 480 μmol) in toluene (5 mL). The mixture was stirred for one hour, subsequently the solvent was removed, the residue was dissolved in a little CH$_2$Cl$_2$ (~5 mL) and the product was precipitated by means of addition of pentane (25 mL). The precipitate was filtered off and dried in vacuo. Yellow solid (417 mg, 81%). $^1$H NMR (400 MHz, CD$_2$Cl$_2$): δ=13.63 (s, 1H), 9.76 (dd, J=4.7, 1.6 Hz, 1H), 9.30 (dd, J=5.1, 1.5 Hz, 1H), 8.26 (dd, J=8.2, 1.6 Hz, 1H), 7.94 (dd, J=8.2, 1.4 Hz, 1H), 7.84 (dd, J=8.0, 1.4 Hz, 6H), 7.72 (d J=8.8 Hz, 1H), 7.61 (dd, J=8.2, 4.7 Hz, 1H), 7.50 (d, J=8.8 Hz, 1H), 7.41 (dd, J=8.2, 5.2 Hz, 1H), 7.23 (tt, J=7.4, 1.4 Hz, 3H), 7.08-7.03 (m, 9H), 7.00 (dd, J=8.0, 1.4 Hz, 6H), 6.80 (t, J=7.4 Hz, 6H), 6.72-6.71 (m, 3H), 4.37 (br s, 1H), 3.66 (br s, 1H), 1.20 (s, 9H), 1.14 (br s, 3H), 0.50 (br s, 6H), −043 ppm (br s, 3H); $^{13}$C NMR (100 MHz, CD$_2$Cl$_2$): δ=304.9, 158.1, 150.2, 149.5, 145.0, 143.3, 141.4, 140.6, 138.6, 137.4, 136.7, 135.5, 135.3, 130.5, 130.1, 130.0, 128.5, 128.3, 128.0, 127.5, 127.4, 127.2, 127.0, 125.2, 124.9, 124.2, 123.1, 49.0, 32.0 ppm; IR (film, cm$^{-1}$): 2936, 2866, 1513, 1423, 1256, 1144, 1106, 1032, 947, 842, 760, 698.

[Mo(CHCMe$_2$Ph)(NAr)(OSiPh$_3$)$_2$(phen)](Ar=2,6-diisopropylphenyl).

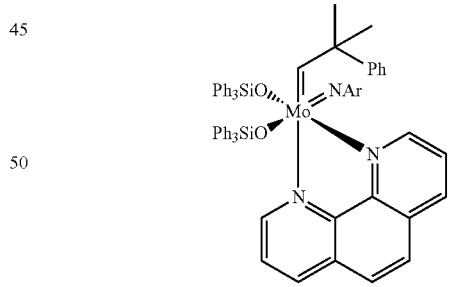

Prepared as described above from Ph$_3$SiOK (300 mg, 955 μmol), [Mo(CHCMe$_2$Ph)(NAr)(OSO$_2$CF$_3$)$_2$(dme)](378 mg, 477 μmol) and 1,10-phenanthroline (86 mg, 477 μmol). Yellow solid (460 mg, 85%). $^1$H NMR (400 MHz, CD$_2$Cl$_2$): δ=13.61 (s, 1H), 9.78 (dd, J=4.7, 1.6 Hz, 1H), 8.22 (dd, J=8.2, 1.5 Hz, 1H), 7.91 (dd, J=5.2, 1.5 Hz, 11H), 7.85 (dd, J=8.0, 1.4 Hz, 6H), 7.76 (dd, J=8.2, 1.5 Hz, 1H), 7.62-7.58 (m, 4H), 7.48 (t, J=7.6 Hz, 2H), 7.36 (t, J=8.8 Hz, 1H), 7.25 (tt, J=7.4, 1.4 Hz, 3H), 7.09-7.02 (m, 10H), 6.91 (dd, J=8.0, 1.4 Hz, 6H), 6.86 (dd, J=5.1, 3.0 Hz, 1H), 6.77 (t, J=7.6 Hz, 6H), 6.74 (m, 3H), 4.53 (br s, 1H), 3.20 (br s, 1H), 2.20 (s, 3H), 1.20 (br s, 3H), 0.93 (s, 3H), 0.56 (br s, 6H), −0.67 ppm (br s, 3H); $^{13}$C NMR (100 MHz, βCD$_2$Cl$_2$): δ=300.2, 157.5, 151.4, 150.2, 149.3, 144.6, 143.2, 141.4, 140.4, 138.3, 137.4, 136.7, 136.3, 135.4, 135.3, 130.5, 129.9, 129.8, 128.6, 128.3, 128.0, 127.8, 127.5, 127.4, 127.2, 127.0, 126.9, 126.1, 125.4, 124.1, 54.6, 31.2, 28.3, 28.2, 22.6 ppm. IR (film, cm$^{-1}$): 3065, 2963, 2866, 1517, 1426, 1333, 1285, 1110, 971, 918, 871, 742, 699.

solution of 2,2'-bipyridine (65 mg, 418 μmol) in Et$_2$O (2 mL) and the mixture was stirred for one hour at room temperature. Subsequently, the solvent was removed and the residue was purified by re-crystallization from pentane at −40° C. After drying in vacuo the desired complex is obtained as orange-red

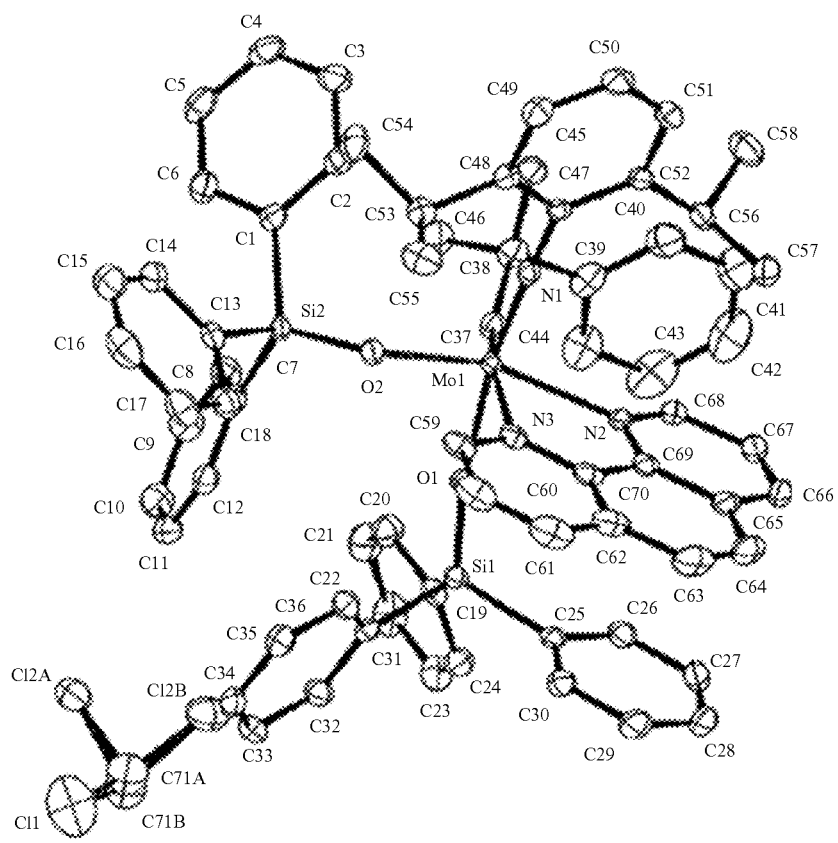

FIG. 3. Structure of Mo(CHCMe$_2$Ph)(NAr)(OSiPh$_3$)$_2$(phen)] (Ar = 2,6-diisopropylphenyl) in the solid state. The crystal contains co-crystallized CH$_2$Cl$_2$.

[Mo(CHCMe$_2$Ph)(NAr)((R)-(+)-tBu$_2$Me$_4$(biphen))(bipy)] (Ar=2,6-diisopropylphenyl).

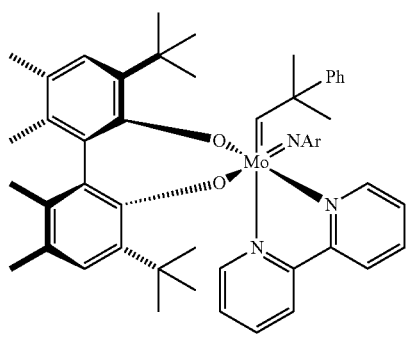

A solution of [Mo(CHCMe$_2$Ph)((R)-(+)-tert-Bu$_2$Me$_4$(biphen)](316 mg, 418 μmol) in Et$_2$O (3 mL) was added to a solid. (282 mg, 74%). $^1$H NMR (400 MHz, CD$_2$Cl$_2$): δ=13.03 (s, 1H), 8.62 (dd, J=5.2, 1.8 Hz, 1H), 7.87 (d, J=8.0 Hz, 1H), 7.79 (d, J=8.2 Hz, 1H), 7.74-7.68 (m, 2H), 7.56 (dd, J=8.5, 1.2 Hz, 2H), 7.36-7.31 (m, 3H), 7.19 (tt, J=7.2, 1.2 Hz, 1H), 6.98 (s, 1H), 6.94 (ddd, J=7.4, 5.2, 1.1 Hz, 1H), 6.83 (ddd, J=7.4, 5.4, 1.2 Hz, 1H), 6.79-6.74 (m, 3H), 6.35 (s, 1H), 4.18 (br s, 1H), 3.65 (br s, 1H), 2.24 (s, 3H), 2.12 (s, 3H), 1.73 (s, 3H), 1.57 (s, 3H), 1.54 (s, 3H), 1.49 (s, 9H), 1.28 (br s, 3H), 1.04 (s, 6H), 0.71 (br s, 3H), 0.68 (s, 9H), −0.01 ppm (br s, 3H); $^{13}$C NMR (100 MHz, CD$_2$Cl$_2$): δ=305.3, 168.6, 162.2, 157.9, 154.4, 151.9, 151.6, 150.7, 150.4, 149.5, 148.8, 148.6, 146.9, 138.7, 138.4, 137.2, 133.8, 133.6, 133.2, 132.4, 132.0, 131.5, 129.2, 128.4, 127.2, 126.4, 125.7, 125.4, 125.3, 125.0, 124.9, 124.8, 122.6, 122.0, 121.2, 35.0, 34.8, 34.5, 32.1, 32.0, 31.5, 29.7, 27.4, 26.4, 25.2, 24.2, 22.6, 20.3, 20.1, 19.9, 16.4, 16.0, 15.8, 14.2 ppm; IR (film, cm$^{-1}$): 2920, 2862, 1738, 1595, 1408, 1261, 1040, 974, 859, 798, 756, 702.

FIG. 4. Structure of [Mo(CHCMe₂Ph)(NAr)((R)-(+)-tBu₂Me₄(biphen))(bipy)] (Ar = 2,6-diisopropylphenyl) in solid state.

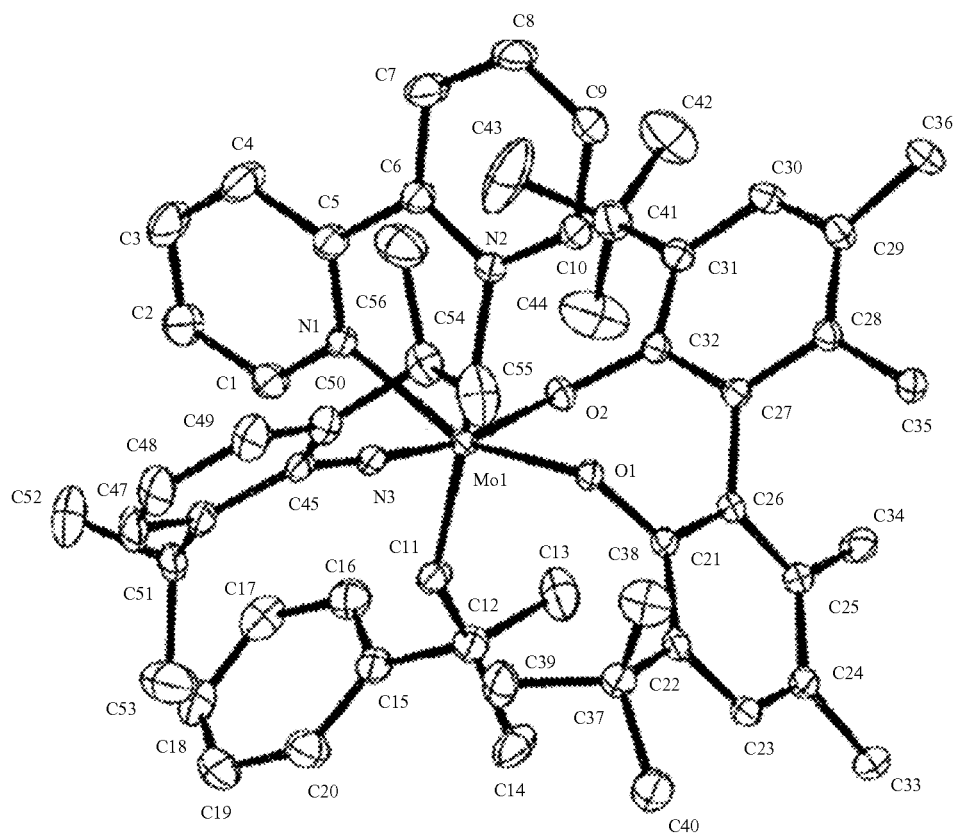

Ring-Closing Olefin Metathesis by Means of [Mo(CHCMe₂Ph)(NAr)(OCMe(CF₃)₂)₂(Phen)] in Presence of ZnCl₂ (Ar=2,6-diisopropylphenyl)).

A solution of [Mo(CHCMe₂Ph)(NAr)(OCMe(CF₃)₂)₂(phen)](24 mg, 25 μmol, 5 mol %) and anhydrous ZnCl₂ (3.4 mg, 25 μmol) in toluene (2.5 mL) was heated for 30 min under argon to 100° C. After this activation phase, the mixture was cooled down to room temperature prior to the addition of diethyl 2,2-diallylmalonate (121 μL, 500 μmol). Subsequently, it was stirred for further 30 min at room temperature, subsequently the solvent was removed and the residue was purified by means of column chromatography. One obtained diethylcyclopent-3-ene-1,1-dicarboxylate as colorless oil (104 mg, 98%). ¹H NMR (400 MHz, CDCl₃): δ=5.59 (s, 2H), 4.19 (q, J=7.1 Hz, 4H), 3.00 (s, 4H), 1.24 ppm (t, J=7.1 Hz, 6H); ¹³C NMR (100 MHz, CDCl₃): δ=172.4, 127.9, 61.6, 59.0, 41.0, 14.2 ppm; IR (film, cm⁻¹): 3463, 2982, 2872, 1728, 1446, 1366, 1248, 1179, 1060, 1015, 951, 695; MS (EI) m/z (%): 212 [M⁺] (25), 166 (45), 138 (100), 111 (41), 93 (39), 79 (56), 66 (76), 55(5), 39 (16), 29 (97); HRMS (ESI): m/z: calculated for C₁₁H₁₆O₄+Na: 235.0946. found: 235.0941. The obtained data correspond to those of literature (T. Kirkland, R. H. Grubbs, *J. Org. Chem.* 1997, 62, 7310-7318).

Diethyl 3,4-dimethylcyclopent-3-ene-1,1-dicarboxylate

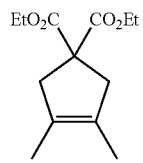

Analogously prepared as colorless oil. ¹H NMR (400 MHz, CDCl₃): δ=4.18 (q, J=7.1 Hz, 4H), 2.92 (s, 4H), 1.58 (s, 6H), 1.23 ppm (t, J=7.1 Hz, 6H); ¹³C NMR (100 MHz, CDCl₃): δ=172.7, 128.2, 122.9, 61.5, 57.3, 46.0, 28.1, 22.6, 14.2, 13.4 ppm; IR (film, cm⁻¹): 3462, 2970, 2859, 1729, 1443, 1366, 1246, 1180, 1071, 1019; MS (EI) m/z (%): 240 [M⁺] (26), 195 (7), 166 (100), 138 (11), 121 (23), 107 (15), 93 (42), 79 (17), 29 (30); HRMS (ESI): m/z: calculated for C₁₃H₂₀O₄+Na: 263.1259. found: 263.1254. The obtained data correspond to those of literature (T. Kirkland, R. H. Grubbs, *J. Org. Chem.* 1997, 62, 7310-7318).

Diethyl 3-tert-butylcyclopent-3-ene-1,1-dicarboxylate

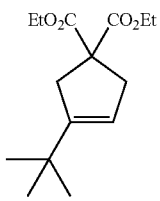 [SMILES: CCOC(=O)C1(C(=O)OCC)CC=C(C(C)(C)C)C1]

Analogously prepared as colorless oil. $^1$H NMR (400 MHz, CDCl$_3$): δ=5.17 (s, 1H), 4.18 (q, J=7.1 Hz, 4H), 2.94 (s, 4H), 1.23 (t, J=7.1 Hz, 6H), 1.04 ppm (s, 9H); $^{13}$C NMR (100 MHz, CDCl$_3$): δ=172.4, 151.1, 117.6, 61.5, 59.6, 40.3, 39.9, 32.8, 29.0, 14.2 ppm; IR (film, cm$^{-1}$): 3462, 2964, 2869, 1730, 1446, 1364, 1245, 1183, 1060, 1024, 815, 737; MS (EI) m/z (%): 268 [M*] (24), 223 (8), 194 (58), 179 (82), 151 (14), 138 (20), 133 (22), 121 (100), 107 (82), 91 (21), 79 (12), 65 (7), 57 (26), 41 (14), 29 (58); HRMS (ESI): m/z: calculated for C$_{15}$H$_{24}$O$_4$+Na: 291.1572. found: 291.1567. The obtained data correspond to those of literature (T. Kirkland, R. H. Grubbs, J. Org. Chem. 1997, 62, 7310-7318).

Diethyl 3-methyl-cyclohept-3-ene-1,1-dicarboxylate

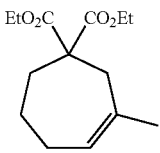 [SMILES: CCOC(=O)C1(C(=O)OCC)CCCC=C(C)C1]

Analogously prepared as colorless oil. $^1$H NMR (400 MHz, CDCl$_3$): δ=5.57 (t, J=6.2 Hz, 1H), 4.16 (q, J=7.1 Hz, 4H), 2.64 (s, 2H), 2.19-2.16 (m, 2H), 2.07-2.03 (m, 2H), 1.75 (s, 3H), 1.65-1.59 (m, 2H), 1.23 ppm (t, J=7.1 Hz, 6H); $^{13}$C NMR (100 MHz, CDCl$_3$): δ=172.0, 135.2, 127.7, 61.2, 55.8, 37.6, 36.9, 28.0, 26.7, 22.9, 14.2 ppm; IR (film, cm$^{-1}$): 3463, 2970, 2862, 1729, 1446, 1366, 1310, 1217, 1090, 1056, 1030; MS (EI) m/z (%): 254 [M$^+$] (15), 208 (20), 180 (22), 173 (100), 163 (14), 152 (7), 135 (15), 127 (28), 107 (33), 91 (9), 79 (11); HRMS (ESI): m/z: calculated for C$_{14}$H$_{22}$O$_4$+Na: 277.1416. found: 277.1410. The obtained data correspond to those of literature (T. Kirkland, R. H. Grubbs, J. Org. Chem. 1997, 62, 7310-7318).

2,2-Dimethyl-6-phenyl-1-oxa-2-silacyclohex-3-ene

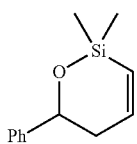

Analogously prepared as colorless oil; the purification was performed by means of Kugelrohr distillation (bp=93-95° C., 0.4 Torr). $^1$H NMR (400 MHz, CDCl$_3$): δ=7.43 (dd, J=8.8, 1.6 Hz, 2H), 7.37 (td, J=8.8, 1.6 Hz, 2H), 7.27 (tt, J=8.8, 1.6 Hz, 1H), 6.86 (ddd, J=14.0, 6.0, 2.4 Hz, 1H), 5.89 (ddd, J=14.0, 2.8, 0.8 Hz, 1H), 5.02 (dd, J=10.0, 3.6 Hz, 1H), 2.47-2.33 (m, 2H), 0.28 (s, 3H), 0.27 ppm (s, 3H); $^{13}$C NMR (100 MHz, CDCl$_3$): δ=147.2, 144.6, 128.5, 127.6, 127.3, 125.7, 73.5, 39.1, 0.0, −0.4 ppm; IR (film, cm$^{-1}$): 2958, 2855, 1587, 1249, 1062, 955, 833, 785, 695; MS (EI) m/z (%): 204 [M$^+$] (43), 189 (5), 130 (100), 111 (5), 98 (40), 83 (25), 75 (6), 61 (5); HRMS (ESI): m/z: calculated for C$_{12}$H$_{16}$OSi: 204.0970. found: 204.0970. The obtained data correspond to those of literature (S. E. Denmark, S.-M. Yang, Org. Lett. 2001, 3, 1749-1752).

2-Benzylbenzofuran

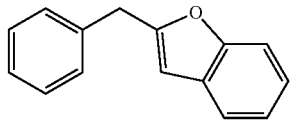 [SMILES: c1ccc(Cc2cc3ccccc3o2)cc1]

Analogously prepared as colorless oil. $^1$H NMR (400 MHz, CDCl$_3$): δ=7.43-7.41 (m, 1H), 7.37-7.35 (m, 1H), 7.30-7.24 (m, 4H), 7.23-7.10 (m, 3H), 6.32 (s, 1H), 4.06 ppm (s, 2H); $^{13}$C NMR (100 MHz, CDCl$_3$): δ=157.9, 155.1, 137.4, 129.1, 128.8, 126.9, 123.6, 122.7, 120.5, 111.1, 103.5, 35.1 ppm; IR (film, cm$^{-1}$): 3029, 2906, 1738, 1585, 1495, 1453, 1251, 1163, 952, 791, 739, 701; MS (EI) m/z (%): 208 [M$^+$] (100), 189 (4), 178 (14), 165 (3), 152 (3), 131 (32), 115 (3), 104 (4), 89 (7), 77 (5), 51 (3); HRMS (ESI): m/z: calculated for C$_{15}$H$_{12}$O: 208.0888. found: 208.0888. The obtained data correspond to those of the literature (O. Fujimura, G. C. Fu, R. H. Grubbs J. Org. Chem. 1994, 59, 4029-4031).

(3R,4R)-3-Azido-4-benzyloxy-2,3,4,7-tetrahydroazepin-1-carboxylic acid tert-butylester

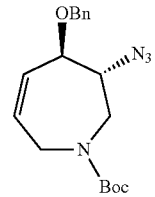 [SMILES: CC(C)(C)OC(=O)N1CC=C[C@@H](OCc2ccccc2)[C@H](N=[N+]=[N-])C1]

A solution of Mo(CHCMe$_2$Ph)(NAr)(OCMe(CF$_3$)$_2$)$_2$ (phen) (8 mg, 9 μmol, 5 mol %) and ZnCl$_2$ (1.2 mg, 9 μmol) in CH$_2$Cl$_2$ (18 mL) was heated for 30 min to 100° C. Subsequently, (2R,3R)-allyl-(2-azido-3-benzyloxy-pent-4-enyl)-carbamic acid tert-butylester (66 mg, 0.177 mmol) was added and the mixture was heated for 30 min under reflux. After removal of the solvent, the residue is purified by means of column chromatography at silica gel (hexane/ethylacetate, 20:1). $^1$H NMR (300 MHz, CD$_2$Cl$_2$): δ=7.40-7.29 (m, 5H), 5.76 (br s, 2H), 4.67 (d, J=11.5 Hz, 1H), 4.55 (d, J=11.5 Hz, 1H), 427-3.97 (m, 2H), 3.85-3.54 (m, 4H), 1.45 (s, 9H); $^{13}$C NMR (75 MHz, CD$_2$Cl$_2$): δ=155.1, 138.3, 131.1, 129.8, 128.7, 128.3, 128.1, 80.5, 79.1, 72.3, 64.0, 48.8, 47.5, 28.4; [α]$^{20}_D$=−26.3 (2.65, CH$_2$Cl$_2$); IR (film, cm$^{-1}$): 3065, 3031, 2976, 2927, 2857, 2108, 1699, 1657, 1496, 1456, 1393, 1366, 1248, 1168, 1135, 1095, 737, 698 cm$^{-1}$; MS (EI) m/z: 344 ([M$^+$], <1), 260 (1), 225 (2), 186 (1), 180 (3), 169 (14), 160 (6), 125 (11), 91 (100), 57 (57); HRMS (ESI) (C$_{18}$H$_{24}$N$_4$O$_3$+H) calculated: 345.1927. found: 345.1921; C$_{18}$H$_{24}$N$_4$O$_3$ (344.41) calculated: C, 62.77; H, 7.02; N, 16.27. found: C, 62.72; H, 6.94; N, 16.19. The obtained data correspond to those of literature (A. Fürstner, O. R Thiel, *J. Org. Chem.* 2000, 65, 1738).

Kinetical Resolution while Using [Mo(CHCMe$_2$Ph)(NAr)((R)-(+)-tBu$_2$Me$_4$(biphen))(bipy)] in Presence of ZnCl$_2$ (Ar=2,6-diisopropylphenyl).

A solution of [Mo(CHCMe$_2$Ph)(NAr)((R)-(+)-tBu$_2$Me$_4$(biphen))(bipy)](31 mg, 33 µmol, 5 mol %) und ZnCl$_2$ (4.5 mg, 33 µmol) in toluene (2.6 mL) was stirred for 30 min at 80° C. After this activation phase, the mixture was cooled down to room temperature and a solution of (6E)-6-Methyl-5-tert-butyldimethylsiloxy-1,6-octadiene (168 mg, 660 µmol) in toluene (4 mL) was added. The mixture was stirred for 80 min in the closed vessel before the reaction was interrupted by addition of MeOH (3 mL). The mixture was concentrated and the brown residue was chromatographically purified. The obtained products have the following spectroscopic properties:

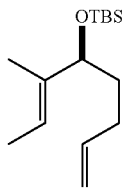

(6E)-6-Methyl-5-tert-butyldimethylsiloxy-1,6-octadiene ee=90% (determined by GC at chiral phase: Ivadex-1/PS086 (dimethyl-pentyl-β-cyclodextrin, 25 m)); $^1$H NMR (400 MHz, CDCl$_3$): δ=5.87-5.77 (m, 1H), 5.38-5.32 (m, 1H), 5.02-4.91 (m, 2H), 3.95 (t, J=7.1 Hz, 1H), 2.10-1.91 (m, 2H), 1.66-1.44 (m, 8H), 0.87 (s, 9H), 0.02 (s, 3H), −0.03 (s, 3H); $^{13}$C NMR (100 MHz, CDCl$_3$): δ=139.1, 138.4, 119.8, 114.3, 78.2, 35.7, 30.3, 26.0, 18.4, 13.1, 10.9, −4.5, −4.8; IR (film, cm$^{-1}$): 2929, 2858, 1738, 1641, 1472, 1361, 1252, 1217, 1071, 909, 833, 772, 665; MS (EI) m/z (%): 254 [M$^+$] (1); 239 (2), 197 (64), 155 (8), 141 (3), 127 (4), 75 (100), 67 (3), 59 (4), 41 (7); HRMS (ESI): m/z: calculated for C$_{15}$H$_{30}$OSi+H, 255.2144. found: 255.2144.

2-Methyl-1-tert-butyldimethylsiloxy-2-cyclopentene

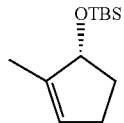

ee=60% (determined by GC at chiral phase: BGB-176/SE-52 (2,3-dimethyl-6-tertbutyldimethylsilyl-β-cyclodextrin, 30 m)); $^1$H NMR (400 MHz, CDCl$_3$): δ=5.47-5.45 (m, 1H), 4.66-4.63 (m, 1H), 2.40-2.32 (m, 1H), 2.28-2.20 (m, 1H), 2.18-2.10 (m, 1H), 1.71 (s, 3H), 1.70-1.63 (m, 1H), 0.92 (s, 9H), 0.10 (s, 3H), 0.09 (s, 3H); $^{13}$C NMR (100 MHz, CDCl$_3$): δ=142.2, 126.9, 80.3, 34.5, 29.8, 26.1, 14.0, −4.3, −4.6; IR (film, cm$^{-1}$): 2930, 2856, 1462, 1354, 1249, 1080, 992, 884, 833, 772, 669; MS (EI) m/z (%): 212 [M$^+$] (9), 197 (2), 137 (3), 155 (32), 75 (100), 59 (3); HRMS (ESI): m/z: calculated for C$_{12}$H$_{24}$OSi: 212.1596. found 212.1596.

The invention claimed is:
1. Metal organic compounds of the general formula I

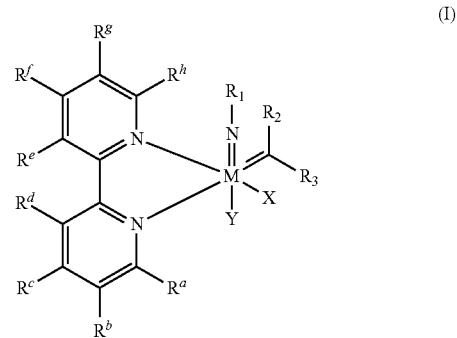

wherein
M is Mo or W,
R$^1$ is C$_1$-C$_{12}$-alkyl or 5- to 18-membered aryl, each of which may be independently substituted with at least one of C$_1$-C$_{12}$-alkyl, 5- to 18-membered aryl, C$_1$-C$_{12}$-alkyloxy, di(C$_1$-C$_4$-alkyl)amino, halogen, trifluoromethyl, cyano, or nitro,
the substituents X, Y may be the same or may be different and are independently selected from at least one of halogen, methanesulfonyloxy, trifluoromethanesulfonyloxy, benzenesulfonyloxy, toluenesulfonyloxy, pyrrolyl, C$_1$-C$_{12}$-alkyloxy, 5- to 18-membered aryloxy, tri(C$_1$-C$_{12}$-alkyl)silyloxy, di(C$_1$-C$_{12}$-alkyl) (C$_6$-C$_{18}$-aryl)silyloxy, (C$_1$-C$_{12}$-alkyl)di(C$_6$-C$_{18}$-aryl)silyloxy, or tris(C$_1$-C$_{12}$-alkyloxy)silyloxy, each of which may be independently substituted with at least one of C$_1$-C$_{12}$-alkyl, 5- to 18-membered aryl, C$_1$-C$_{12}$-alkoxy, di-(C$_1$-C$_4$-alkyl)amino, halogen, trifluoromethyl, cyano, or nitro,
R$^2$ is H, C$_1$-C$_{12}$-alkyl or 5- to 18-membered aryl, each of which may be independently substituted with at least one of C$_1$-C$_{12}$-alkyl, 5- to 18-membered aryl, C$_1$-C$_{12}$-alkyloxy, di(C$_1$-C$_4$-alkyl)amino, halogen, trifluoromethyl, cyano, or nitro,
R$^3$ is C$_1$-C$_{12}$-alkyl or 5- to 18-membered aryl, each of which may be independently substituted with at least one of C$_1$-C$_{12}$-alkyl, 5- to 18-membered aryl, C$_1$-C$_{12}$-alkyloxy, di(C$_1$-C$_4$-alkyl)amino, halogen, trifluoromethyl, cyano, or nitro,
R$^a$, R$^b$, R$^c$, R$^d$, R$^e$, R$^f$, R$^g$, R$^h$ may be the same or may be different and each is independently selected from at least one of H, halogen, nitro, cyano, trifluoromethyl, C$_1$-C$_{12}$-alkoxycarbonyl, C$_1$-C$_{12}$-alkyl, 5- to 18-membered aryl, C$_1$-C$_{12}$-alkyloxy, or di-(C$_1$-C$_4$-alkyl)amino, each of which may be independently substituted with at least one of C$_1$-C$_{12}$-alkyl, 5- to 18-membered aryl, C$_1$-C$_{12}$-alkyloxy, di-(C$_1$-C$_4$-alkyl)amino, halogen, trifluoromethyl, cyano, or nitro, or groups R$^d$ and R$^e$ may be connected to each other to form a 5- to 8-membered ring.

2. Metal complexes according to claim 1, wherein R$^d$ and R$^e$ are a group R$^{48}$, which is selected from at least one of CR$^{49}$R$^{50}$, CR$^{51}$=CR$^{52}$, CR$^{53}$R$^{54}$—CR$^{55}$R$^{56}$, CR$^{57}$R$^{58}$—CR$^{59}$R$^{60}$—CR$^{61}$R$^{62}$, CR$^{62}$R$^{63}$=CR$^{64}$R$^{65}$R$^{67}$, CR$^{69}$R$^{70}$—CR$^{71}$R$^{72}$—CR$^{73}$R$^{74}$—CR$^{75}$CR$^{76}$, CR$^{77}$=CR$^{78}$—CR$^{79}$R$^{80}$—CR$^{81}$CR$^{82}$ or CR$^{83}$R$^{84}$—CR$^{85}$=CR$^{87}$—CR$^{88}$CR$^{89}$, wherein R$^{49}$, R$^{50}$, R$^{51}$, R$^{52}$, R$^{53}$, R$^{54}$, R$^{55}$, R$^{56}$, $R^{57}, R^{58}, R^{59}, R^{60}, R^{61}, R^{62}, R^{63}, R^{64}, R^{65}, R^{66}, R^{67}, R^{68}, R^{69}, R^{70}, R^{71}, R^{72}, R^{73}, R^{74}, R^{75}, R^{76}, R^{77}, R^{78}, R^{79}, R^{80}, R^{81}, R^{82}, R^{83}, R^{84}, R^{85}, R^{86}, R^{87}, R^{88}$ and $R^{89}$ are independently selected from one another and have the same definition as $R^a$.

3. Metal organic complexes according to claim 1, characterized in that they represent compounds of the general formula 2:

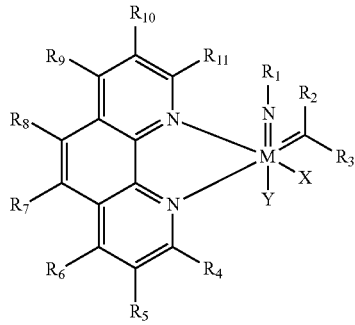

wherein $R^1, R^2, R^3$, X and Y are as defined in claim 1, and $R^4, R^5, R^6, R^7, R^8, R^9, R^{10}, R^{11}$ may be the same or may be different and each is independently selected from at least one of H, halogen, nitro, cyano, trifluoromethyl, $C_1$-$C_{12}$-alkoxycarbonyl, $C_1$-$C_{12}$-alkyl, 5- to 18-membered aryl, $C_1$-$C_{12}$-alkyloxy, or di-($C_1$-$C_4$-alkyl)amino, each of which may be independently substituted with at least one of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, or nitro.

4. Metal organic compounds according to claim 1, characterized in that they represent compounds of the general formula 9:

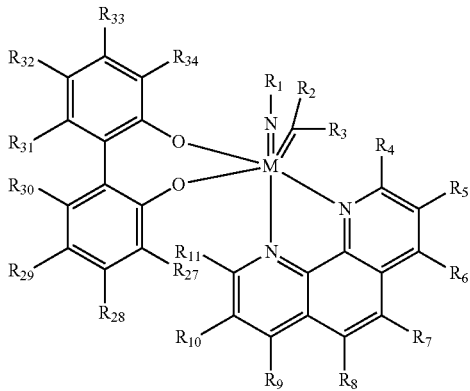

wherein

M, $R^1, R^2$, and $R^3$ are as defined in claim 1, $R^4, R^5, R^6, R^7, R^8, R^9, R^{10}, R^{11}$ may be the same or may be different and each is independently selected from at least one of H, halogen, nitro, cyano, trifluoromethyl, $C_1$-$C_{12}$-alkoxycarbonyl, $C_1$-$C_{12}$-alkyl, 5- to 18-membered aryl, $C_1$-$C_{12}$-alkyloxy, or di-($C_1$-$C_4$-alkyl)amino, each of which may be independently substituted with at least one of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, or nitro, and $R^{27}, R^{28}, R^{29}, R^{30}, R^{31}, R^{32}, R^{33}, R^{34}$ may be the same or may be different and each is independently selected from at least one of H, halogen, nitro, cyano, trifluoromethyl, $C_1$-$C_{12}$-alkoxycarbonyl, $C_1$-$C_{12}$-alkyl, 5- to 18-membered aryl, $C_1$-$C_{12}$-alkyloxy, or di-($C_1$-$C_4$-alkyl)amino, each of which may be independently substituted with at least one of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, or nitro.

5. Metal organic compounds according to claim 1, characterized in that they represent compounds of the general formula 10:

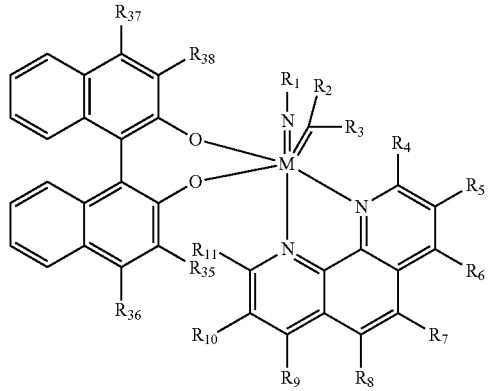

wherein

M, $R^1, R^2$, and $R^3$ are as defined in claim 1, $R^4, R^5, R^6, R^7, R^8, R^9, R^{10}$ and $R^{11}$ may be the same or may be different and each is independently selected from at least one of H, halogen, nitro, cyano, trifluoromethyl, $C_1$-$C_{12}$-alkoxycarbonyl, $C_1$-$C_{12}$-alkyl, 5- to 18-membered aryl, $C_1$-$C_{12}$-alkyloxy, or di-($C_1$-$C_4$-alkyl)amino, each of which may be independently substituted with at least one of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, or nitro, and $R^{35}, R^{36}, R^{37}, R^{38}$ may be the same or may be different and each is independently selected from at least one of H, halogen, nitro, cyano, trifluoromethyl, $C_1$-$C_{12}$-alkyl, 5- to 18-membered aryl, $C_1$-$C_{12}$-alkyloxy, di-($C_1$-$C_4$-alkyl)amino, tri($C_1$-$C_{12}$-alkyl)silyl, di($C_1$-$C_{12}$-alkyl)($C_6$-$C_{18}$-aryl)silyl, or ($C_1$-$C_{12}$-alkyl)di($C_6$-$C_{18}$-aryl)silyl, each of which may be independently substituted with at least one of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, or nitro.

6. Metal organic compounds according to claim 1, characterized in that they represent compounds of the general formula 17:

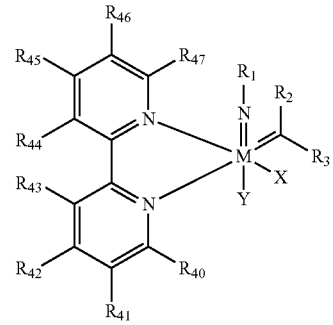

wherein $R^1, R^2, R^3$, X and Y are as defined in claim 1 and $R^{40}, R^{41}, R^{42}, R^{43}, R^{44}, R^{45}, R^{46}, R^{47}$ may be the same or may be different and each is independently selected from at least one of H, halogen, nitro, cyano, trifluoromethyl, $C_1$-$C_{12}$-alkoxycabonyl, $C_1$-$C_{12}$-alkyl, 5- to 18-membered aryl, $C_1$-$C_{12}$-alkyloxy, or di-($C_1$-$C_4$-alkyl)amino, each of which may be independently substituted with at least one of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, or nitro.

7. Metal organic compounds according to claim 1, characterized in that they represent compounds of the general formula 24:

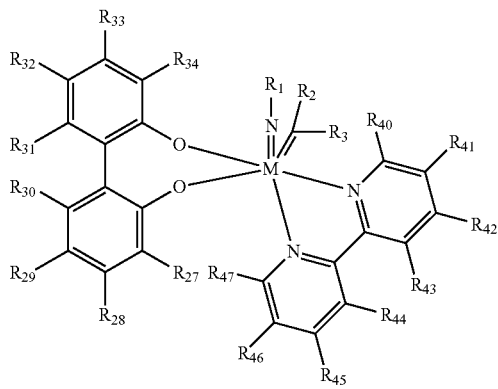

24 wherein

M, $R^1$, $R^2$, and $R^3$ are as defined in claim 1, $R^{40}$, $R^{41}$, $R^{42}$, $R^{43}$, $R^{44}$, $R^{45}$, $R^{46}$ and $R^{47}$ may be the same or may be different and each is independently selected from at least one of H, halogen, nitro, cyano, trifluoromethyl, $C_1$-$C_{12}$-alkoxycabonyl, $C_1$-$C_{12}$-alkyl, 5- to 18-membered aryl, $C_1$-$C_{12}$-alkyloxy, or di-($C_1$-$C_4$-alkyl)amino, each of which may be independently substituted with at least one of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, or nitro, and $R^{27}$, $R^{28}$, $R^{29}$, $R^{30}$, $R^{31}$, $R^{32}$, $R^{33}$, $R^{34}$ may be the same or may be different and each is independently selected from at least one of H, halogen, nitro, cyano, trifluoromethyl, $C_1$-$C_{12}$-alkoxycabonyl, $C_1$-$C_{12}$-alkyl, 5- to 18-membered aryl, $C_1$-$C_{12}$-alkyloxy, or di-($C_1$-$C_4$-alkyl)amino, each of which may be independently substituted with at least one of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, or nitro.

8. Metal organic compounds according to claim 1, characterized in that they represent compounds of the general formula 25:

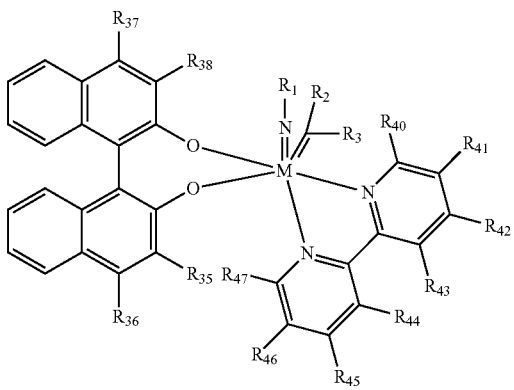

25 wherein

M, $R^1$, $R^2$, and $R^3$ are as defined in claim 1, $R^{40}$, $R^{41}$, $R^{42}$, $R^{43}$, $R^{44}$, $R^{45}$, $R^{46}$ and $R^{47}$ may be the same or may be different and each is independently selected from at least one of H, halogen, nitro, cyano, trifluoromethyl, $C_1$-$C_{12}$-alkoxycabonyl, $C_1$-$C_{12}$-alkyl, 5- to 18-membered aryl, $C_1$-$C_{12}$-alkyloxy, or di-($C_1$-$C_4$-alkyl)amino, each of which may be independently substituted with at least one of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, or nitro, and $R^{35}$, $R^{36}$, $R^{37}$, $R^{38}$ may be the same or may be different and each is independently selected from at least one of H, halogen, nitro, cyano, trifluoromethyl, $C_1$-$C_{12}$-alkyl, 5- to 18-membered aryl, $C_1$-$C_{12}$-alkyloxy, di-($C_1$-$C_4$-alkyl)amino, tri($C_1$-$C_{12}$-alkyl)silyl, di($C_1$-$C_{12}$-alkyl)($C_6$-$C_{18}$-aryl)silyl, or ($C_1$-$C_{12}$-alkyl)di($C_6$-$C_{18}$-aryl)silyl, each of which may be independently substituted with at least one of $C_1$-$C_{12}$-alkyl, 5- to 18-membered aryl, $C_1$-$C_{12}$-alkyloxy, di-($C_1$-$C_4$-alkyl)amino, halogen, trifluoromethyl, cyano, or nitro.

9. A method of preparing metal complexes of the general formula I

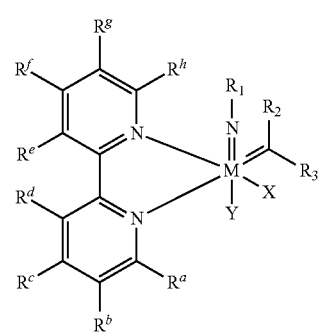

(I)

wherein M, X, Y, $R^1$, $R^2$, $R^3$, $R^a$, $R^b$, $R^c$, $R^d$, $R^e$, $R^f$, $R^g$, $R^h$ are as defined in claim 1, in which a compound of formula 32

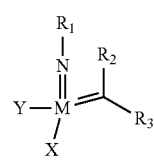

32 wherein M, X, Y, $R_1$, $R_2$, $R_3$ are as defined in claim 1, is reacted with a compound of the general formula II

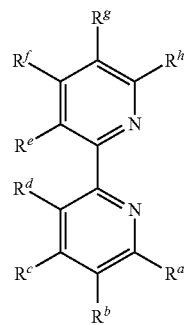
(II)

wherein $R^a$, $R^b$, $R^c$, $R^d$, $R^e$, $R^f$, $R^g$, $R^h$ are as defined in claim 1.

10. A method for olefin metathesis, comprising:
activating a solution comprising the compound of the general formula I

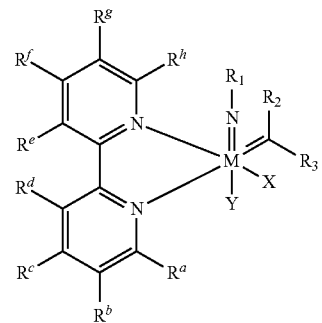
(I)

wherein M, X, Y, $R^1$, $R^2$, $R^3$, $R^a$, $R^b$, $R^c$, $R^d$, $R^e$, $R^f$, $R^g$, $R^h$ are as defined in claim 1; and
adding an olefin to the solution.

* * * * *

UNITED STATES PATENT AND TRADEMARK OFFICE
CERTIFICATE OF CORRECTION

Page 1 of 2

PATENT NO. : 9,233,362 B2
APPLICATION NO. : 14/001811
DATED : January 12, 2016
INVENTOR(S) : Alois Furstner et al.

It is certified that error appears in the above-identified patent and that said Letters Patent is hereby corrected as shown below:

Specification

Column 4, Line 9 reads, "... $R^{66}$, $R^{67}R^{68}$, $R^{69}$, ..." which should read "... $R^{66}$, $R^{67}$, $R^{68}$, $R^{69}$, ..."

Column 20, Line 36 reads, "... $FeX_2$, $FeX_3$, $COX_2$, ..." which should read "... $FeX_2$, $FeX_3$, $CoX_2$, ..."

Column 20, Line 45 reads, "... ZnI2, Zn(triflate)$_2$, ..." which should read "... ZnI2, Zn(triflate)$_2$, ..."

Column 21, Scheme 3 description, Line 2 reads, "... $ZnCl_2$ as particularyl preferred additive ..." which should read "... $ZnCl_2$ as particularly preferred additive ..."

Column 26, Line 61 reads, "... (dd, J=5.2, 1.5 Hz, 11H), ..." which should read "... (dd, J=5.2, 1.5 Hz, 1H), ..."

Column 29, Line 64 reads, "... 235.0946. found: ..." which should read "... 235.0946; found: ..."

Column 30, Line 64 reads, "... 263.1259. found: ..." which should read "... 263.1259; found: ..."

Column 31, Line 24 reads, "... 291.1572. found: ..." which should read "... 291.1572; found: ..."

Column 31, Line 42 reads, "... 6=172.0, 135.2, ..." which should read "... Δ=172.0, 135.2, ..."

Signed and Sealed this
Seventh Day of June, 2016

Michelle K. Lee
*Director of the United States Patent and Trademark Office*

CERTIFICATE OF CORRECTION (continued)
U.S. Pat. No. 9,233,362 B2

Column 31, Line 48 reads, "... 277.1416. found: ..." which should read "... 277.1416; found: ..."

Column 32, Lines 7-8 reads, "... 204.0970. found: ..." which should read "... 204.0970; found: ..."

Column 32, Line 31 reads, "... 208.888. found: ..." which should read "... 208.888; found: ..."

Column 32, Line 62 reads, "... $[\alpha]^{20}_D$=6-26.3 ..." which should read "... $[\alpha]^{20}_D$=-26.3 ..."

Column 32, Line 67 reads, "... 345.1927. found: ..." which should read "... 345.1927; found: ..."

Column 33, Line 1 reads, "... N, 16.27. found: ..." which should read "... N, 16.27, found: ..."

Column 33, Line 46 reads, "... 255.2144. found: ..." which should read "... 255.2144; found: ..."

Column 34, Line 2 reads, "... 212.1596. found: ..." which should read "... 212.1596; found: ..."